(12) United States Patent
Andrews et al.

(10) Patent No.: US 6,630,504 B2
(45) Date of Patent: Oct. 7, 2003

(54) PHENOXYPHENYLHETEROCYCLYL DERIVATIVES AS SSRIS

(75) Inventors: Mark David Andrews, County of Kent (GB); David Hepworth, County of Kent (GB); Donald Stuart Middleton, County of Kent (GB); Alan Stobie, County of Kent (GB)

(73) Assignee: Pfizer Inc., New York, NY (US)

( * ) Notice: Subject to any disclaimer, the term of this patent is extended or adjusted under 35 U.S.C. 154(b) by 0 days.

(21) Appl. No.: 09/939,475

(22) Filed: Aug. 24, 2001

(65) Prior Publication Data

US 2002/0183303 A1 Dec. 5, 2002

Related U.S. Application Data

(60) Provisional application No. 60/285,728, filed on Apr. 23, 2001, and provisional application No. 60/240,326, filed on Oct. 13, 2000.

(30) Foreign Application Priority Data

Aug. 31, 2000 (GB) .............................................. 0021594
Mar. 7, 2001 (GB) .............................................. 0105634

(51) Int. Cl.[7] ...................... A61K 31/42; C07D 207/02; A61P 43/00
(52) U.S. Cl. ....................... 514/423; 514/429; 548/531; 548/540; 548/565; 548/577
(58) Field of Search ................. 548/577, 565, 548/540, 531; 514/429, 423

(56) References Cited

U.S. PATENT DOCUMENTS

| | | | |
|---|---|---|---|
| 4,161,529 A | 7/1979 | Beregi et al. | |
| 5,190,965 A | 3/1993 | Ruigt et al. | |
| 5,430,063 A | 7/1995 | Ruigt et al. | |

FOREIGN PATENT DOCUMENTS

| | | | | |
|---|---|---|---|---|
| EP | 0030081 | 3/1983 | ......... | C07C/87/457 |
| EP | 0394043 | 4/1990 | | |
| EP | 0402097 | 6/1990 | | |
| GB | 2276162 | 9/1994 | ......... | C07D/211/26 |
| WO | WO 9623783 | 8/1996 | | |
| WO | WO 9637204 | 11/1996 | | |
| WO | WO 9717325 | 5/1997 | | |
| WO | WO 0050380 | 8/2000 | | |
| WO | WO 0127068 | 4/2001 | | |

Primary Examiner—Joseph K. McKane
Assistant Examiner—Andrea D. Small
(74) Attorney, Agent, or Firm—Peter C. Richardson; Gregg C. Benson; A. Dean Olson

(57) ABSTRACT

The invention provides compounds of general formula (I) wherein $R^1$ is H or $C_1$–$C_6$ alkyl; $R^2$ and $R^3$, together with the interconnecting atoms form a 4 to 8-membered saturated ring containing one or two heteroatoms (including the nitrogen to which $R^2$ is attached) wherein a second heteroatom, if present, is selected from oxygen, nitrogen and sulfur, with the proviso that said ring cannot contain two adjacent heteroatoms; Z is $CF_3$, $OCF_3$, $C_1$–$C_6$alkylthio or $C_1$–$C_6$alkoxy; Y is hydrogen, halogen, —$OR^a$, $R^a$ or $C_1$–$C_6$alkylthio, and wherein $R^a$ is $C_1$–$C_4$ alkyl optionally substituted with fluorine atoms; or when Z and Y are attached para and meta to the ether linkage linking rings A and B, Z and Y are linked so that, together with the interconnecting atoms, Z and Y form a fused 5 to 7-membered carbocyclic or heterocyclic ring which may be saturated, unsaturated or aromatic, and wherein when Z and Y form a heterocyclic ring, in addition to carbon atoms, the linkage contains one or two heteroatoms independently selected from oxygen, sulfur and nitrogen; and Z and Y together do not form a fused phenyl ring; $R^4$ and $R^5$, which may be the same or different, are: A—X, wherein A═—CH═CH— or —$(CH_2)_p$— where p is 0, 1 or 2; X is hydrogen, F, Cl, Br, I, $CONR^6R^7$, $SO_2NR^6R^7$, $SO_2NHC(═O)R^6$, OH, $C_{1-4}$alkoxy, $NR^8SO_2R^9$, $NO_2$, $NR^6R^{11}$, CN, $CO_2R^{10}$, CHO, $SR^{10}$, $S(O)R^9$ or $SO_2R^{10}$; or a 5- or 6-membered heterocyclic ring containing 1, 2 or 3 heteroatoms selected from N, S and O, optionally substituted independently by one or more $R^{13}$; wherein $R^{13}$ is hydroxy, $C_1$–$C_4$alkoxy, F, $C_1$–$C_6$alkyl, haloalkyl, haloalkoxy, —$NH_2$, —$NH(C_1$–$C_6$alkyl) or —$N(C_1$–$C_6$alkyl)$_2$.

(I)

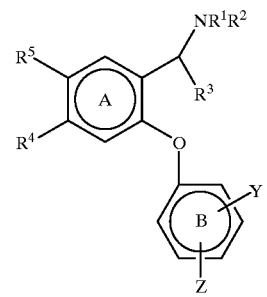

16 Claims, No Drawings

PHENOXYPHENYLHETEROCYCLYL DERIVATIVES AS SSRIS

This application claims priority from co-pending U.S. Provisional Application No. 60/240,326 filed Oct. 13, 2000 and U.S. Provisional Application No. 60/285,728 filed Apr. 23, 2001.

This invention relates to novel diphenyl ether compounds which inhibit monoamine re-uptake. In particular compounds of the present invention exhibit activity as selective serotonin re-uptake inhibitors (SSRIs) and have utility therefore in a variety of therapeutic areas. Notably the compounds of the present invention are useful in the treatment or prevention of a variety of disorders, including those in which the regulation of monoamine transporter function is implicated, such as depression, attention deficit hyperactivity disorder, obsessive-compulsive disorder, post-traumatic stress disorder, substance abuse disorders and sexual dysfunction including premature ejaculation, and to pharmaceutical formulations containing such compounds.

According to a first aspect, the invention provides a compound of general formula (I), pharmaceutically acceptable salts, solvates or polymorphs thereof;

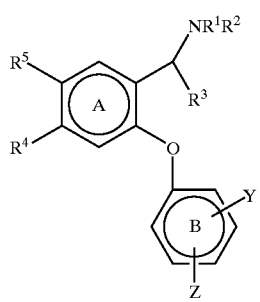

(I)

wherein:

$R^1$ is H or $C_1$–$C_6$ alkyl;

$R^2$ and $R^3$, together with the interconnecting atoms form a 4 to 8-membered saturated ring containing one or two heteroatoms (including the nitrogen to which $R^2$ is attached) wherein a second heteroatom, if present, is selected from oxygen, nitrogen and sulfur, with the proviso that said ring cannot contain two adjacent heteroatoms;

Z is $CF_3$, $OCF_3$, $C_1$–$C_6$alkylthio or $C_1$–$C_6$alkoxy;

Y is hydrogen, halogen, —$OR^a$, $R^a$ or $C_1$–$C_6$alkylthio, and wherein $R^a$ is $C_1$–$C_4$ alkyl optionally substituted with fluorine atoms;

or when Z and Y are attached para and meta to the ether linkage linking rings A and B, Z and Y are linked so that, together with the interconnecting atoms, Z and Y form a fused 5 to 7-membered carbocyclic or heterocyclic ring which may be saturated, unsaturated or aromatic, and wherein when Z and Y form a heterocyclic ring, in addition to carbon atoms, the linkage contains one or two heteroatoms independently selected from oxygen, sulfur and nitrogen;

$R^4$ and $R^5$, which may be the same or different, are:

A—X, wherein A=—CH=CH— or —$(CH_2)_p$— where p is 0, 1 or 2; X is hydrogen, F, Cl, Br, I, $CONR^6R^7$, $SO_2NR^6R^7$, $SO_2NHC(=O)R^6$, OH, $C_{1-4}$alkoxy, $NR^8SO_2R^9$, $NO_2$, $NR^6R^{11}$, CN, $CO_2R^{10}$, CHO, $SR^{10}$, $S(O)R^9$ or $SO_2R^{10}$; $R^6$, $R^7$, $R^8$ and $R^{10}$ which may be the same or different, are hydrogen or $C_{1-6}$alkyl optionally substituted independently by one or more $R^{12}$; $R^9$ is $C_{1-6}$ alkyl optionally substituted independently by one or more $R^{12}$; $R^{11}$ is hydrogen, $C_{1-6}$ alkyl optionally substituted independently by one or more $R^{12}$, $C(O)R^6$, $CO_2R^9$, $C(O)NHR^6$ or $SO_2NR^6R^7$; $R^{12}$ is F (preferably up to 3), OH, $CO_2H$, $C_{3-6}$cycloalkyl, $NH_2$, $CONH_2$, $C_{1-6}$alkoxy, $C_{1-6}$alkoxycarbonyl or a 5- or 6-membered heterocyclic ring containing 1, 2 or 3 heteroatoms selected from N, S and O optionally substituted independently by one or more $R^{13}$; or $R^6$ and $R^7$, together with the nitrogen to which they are attached, form a 4-, 5- or 6-membered heterocyclic ring optionally substituted independently by one or more $R^{13}$; or a 5- or 6-membered heterocyclic ring containing 1, 2 or 3 heteroatoms selected from N, S and O, optionally substituted independently by one or more $R^{13}$; wherein $R^{13}$ is hydroxy, $C_1$–$C_4$alkoxy, F, $C_1$–$C_6$alkyl, haloalkyl, haloalkoxy, —$NH_2$, —$NH(C_1$–$C_6$alkyl) or —$N(C_1$–$C_6$alkyl)_2$.

Unless otherwise indicated, any alkyl group may be straight or branched and is of 1 to 6 carbon atoms, preferably 1 to 4 and particularly 1 to 3 carbon atoms.

Unless otherwise indicated, any heterocyclyl group contains 5 to 7 ring-atoms up to 4 of which may be hetero-atoms such as nitrogen, oxygen and sulfur, and may be saturated, unsaturated or aromatic. Examples of heterocyclyl groups are furyl, thienyl, pyrrolyl, pyrrolinyl, pyrrolidinyl, imidazolyl, dioxolanyl, oxazolyl, thiazolyl, imidazolyl, imidazolinyl, imidazolidinyl, pyrazolyl, pyrazolinyl, pyrazolidinyl, isoxazolyl, isothiazolyl, oxadiazolyl, triazolyl, thiadiazolyl, pyranyl, pyridyl, piperidinyl, dioxanyl, morpholino, dithianyl, thiomorpholino, pyridazinyl, pyrimidinyl, pyrazinyl, piperazinyl, sulfolanyl, tetrazolyl, triazinyl, azepinyl, oxazepinyl, thiazepinyl, diazepinyl and thiazolinyl. In addition, the term heterocyclyl includes fused heterocyclyl groups, for example benzimidazolyl, benzoxazolyl, imidazopyridinyl, benzoxazinyl, benzothiazinyl, oxazolopyridinyl, benzofuranyl, quinolinyl, quinazolinyl, quinoxalinyl, dihydroquinazolinyl, benzothiazolyl, phthalimido, benzofuranyl, benzodiazepinyl, indolyl and isoindolyl. The term heterocyclic should be similarly construed.

Unless otherwise indicated, any carbocyclyl group contains 3 to 8 ring-atoms, and may be saturated, unsaturated or aromatic. Preferred saturated carbocyclyl groups are cyclopropyl, cyclopentyl or cyclohexyl. Preferred unsaturated carbocyclyl groups contain up to 3 double bonds. A preferred aromatic carbocyclyl group is phenyl. The term carbocyclic should be similarly construed. In addition, the term carbocyclyl includes any fused combination of carbocyclyl groups, for example naphthyl, phenanthryl, indanyl and indenyl.

Halo means fluoro, chloro, bromo or iodo.

Preferably $R^1$ is hydrogen or methyl (more preferably hydrogen).

Preferably $R^2$ and $R^3$, together with the interconnecting atoms, form a pyrrolidine ring.

Preferably at least one of Z or Y is para to the ether linkage linking ring A and ring B and is not hydrogen. More preferably the other Z or Y is meta to the ether linkage linking ring A and ring B.

Preferably Z is $CF_3$, $OCF_3$, SMe, SEt or OMe;

Y is hydrogen, F, Cl, Br, methyl, ethyl, OMe, SMe or SEt;

or when Z and Y are attached para and meta to the ether linkage linking rings A and B, Z and Y are linked so that, together with the interconnecting atoms, Z and Y form a fused 5 or 6-membered carbocyclic or heterocyclic ring which may be saturated, unsaturated or aromatic, and wherein when Z and Y form a heterocyclic ring, in addition to carbon atoms, the linkage contains one or two heteroatoms independently selected from oxygen, sulfur and nitrogen (preferred linkages forming the fused ring are —(CH$_2$)$_3$—, —S(CH$_2$)$_2$—, —CH$_2$S—CH$_2$—, —SCH=N—, —(CH$_2$)$_4$—, —S(CH$_2$)$_2$O—, —N=CH=CH=CH—, —CH=N—CH=N— and —CH=CH—N=CH—, wherein either end of these linkages can be attached para to the ether linkage).

Preferably R$^4$ and R$^5$ are not both hydrogen.

Preferably R$^4$ and R$^5$, which may be the same or different, are:

—(CH$_2$)$_p$—X, where p is 0, 1 or 2 (preferably 0 or 1); X is hydrogen, hydroxy, CONR$^6$R$^7$, SO$_2$NR$^6$R$^7$, NR$^8$SO$_2$R$^9$, SR$^{10}$, SOR$^9$ or SO$_2$R$^{10}$ wherein R$^6$, R$^7$, R$^8$, R$^9$ and R$^{10}$ are as defined in the first aspect; or a 5- or 6-membered heterocyclic ring containing 1, 2 or 3 heteroatoms selected from N, S and O (preferably oxadiazolyl, triazolyl, imidazolyl, oxazolyl, pyrazolyl, pyridinyl or pyrimidinyl).

More preferably R$^4$ and R$^5$, which may be the same or different, are:

—(CH$_2$)$_p$—X, where p is 0 or 1; X is hydrogen, hydroxy, CONR$^6$R$^7$, SO$_2$NR$^6$R$^7$ or NR$^8$SO$_2$R$^9$; wherein R$^6$ and R$^7$, which may be the same or different, are hydrogen or C$_1$–C$_3$alkyl optionally substituted by hydroxy, —CONH$_2$ or C$_1$–C$_3$alkoxy (preferably methoxy); R$^8$ is hydrogen, hydroxyethyl or methyl; or R$^9$ is methyl, ethyl, isopropyl, trifluoromethyl or methoxyethyl; or triazolyl, imidazolyl or pyrazolyl.

More preferably still R$^4$ is hydrogen.

Preferably R$^6$ and R$^7$, which may be the same or different, are hydrogen, C$_1$–C$_3$alkyl optionally substituted by hydroxy, —CONH$_2$ or C$_1$–C$_3$alkoxy (preferably methoxy). More preferably R$^6$ and R$^7$, which may be the same or different, are hydrogen or methyl, more preferably still hydrogen.

When present, R$^{12}$ is preferably oxadiazolyl, triazolyl, imidazolyl, oxazolyl, pyrazolyl, pyridinyl or pyrimidinyl. More preferably triazolyl, imidazolyl or pyrazolyl.

Preferably R$^{11}$ is hydrogen or C$_{1-6}$ alkyl.

Preferably R$^8$ is hydrogen, hydroxyethyl or methyl. More preferably hydrogen.

Preferably R$^9$ is methyl, ethyl, isopropyl, trifluoromethyl or methoxyethyl. More preferably methyl or ethyl (preferably methyl).

Preferably R$^{10}$ is methyl or ethyl.

Preferably p is 1 or 0, more preferably 0.

Preferably

R$^1$ is hydrogen or methyl;

R$^2$ and R$^3$, together with the interconnecting atoms form a 4 to 8-membered saturated ring containing one or two heteroatoms (including the nitrogen to which R$^2$ is attached) wherein a second heteroatom, if present, is selected from oxygen, nitrogen and sulfur, with the proviso that said ring cannot contain two adjacent heteroatoms;

at least one of Z or Y is para to the ether linkage linking rings A and B and is not hydrogen; when Z and Y are attached para and meta to the ether linkage linking rings A and B, Z and Y are linked so that, together with the interconnecting atoms, Z and Y form a fused 5 to 7-membered carbocyclic or heterocyclic ring which may be saturated, unsaturated or aromatic, and wherein when Z and Y form a heterocyclic ring, in addition to carbon atoms, the linkage contains one or two heteroatoms independently selected from oxygen, sulfur and nitrogen; and R$^4$ and R$^5$, which may be the same or different, are —(CH$_2$)$_p$—X, where p is 0 or 1; X is hydrogen, hydroxy, CONR$^6$R$^7$, SO$_2$NR$^6$R$^7$, NR$^8$SO$_2$R$^9$, SR$^{10}$, SOR$^9$ or SO$_2$R$^{10}$ and wherein R$^6$ and R$^7$, which may be the same or different, are hydrogen, C$_1$–C$_3$alkyl optionally substituted by hydroxy, —CONH$_2$ or C$_1$–C$_3$alkoxy (preferably methoxy); or R$^6$ and R$^7$, together with the nitrogen to which they are attached, may form a morpholine, pyrrolidine or piperidine ring each of which may be substituted by OH or CONH$_2$; R$^8$ is hydrogen, hydroxyethyl or methyl (preferably hydrogen); R$^9$ is methyl, ethyl, isopropyl, trifluoromethyl or methoxyethyl; and R$^{10}$ is methyl or ethyl; or an oxadiazolyl, triazolyl, imidazolyl, oxazolyl, pyrazolyl, pyridinyl or pyrimidinyl group.

More preferably

R$^1$ is hydrogen or methyl;

R$^2$ and R$^3$, together with the interconnecting atoms, form a pyrrolidine ring;

Z is CF$_3$, OCF$_3$, SMe, SEt or OMe;

Y is hydrogen, F, Cl, Br, methyl, ethyl, OMe, SMe or SEt; wherein at least one of Z or Y is para to the ether linkage linking ring A and ring B and is not hydrogen and the other Z or Y is meta to the ether linkage linking ring A and ring B; or when Z and Y are attached para and meta to the ether linkage linking rings A and B, Z and Y are linked so that, together with the interconnecting atoms, Z and Y form a fused 5 or 6-membered carbocyclic or heterocyclic ring which may be saturated, unsaturated or aromatic, and wherein when Z and Y form a heterocyclic ring, in addition to carbon atoms, the linkage contains one or two heteroatoms independently selected from oxygen, sulfur and nitrogen; and R$^4$ and R$^5$, which may be the same or different, are —(CH$_2$)$_p$—X, where p is 0 or 1; X is hydrogen, hydroxy, CONR$^6$R$^7$, SO$_2$NR$^6$R$^7$ or NR$^8$SO$_2$R$^9$; wherein R$^6$ and R$^7$, which may be the same or different, are hydrogen, C$_1$–C$_3$alkyl optionally substituted by hydroxy, —CONH$_2$ or C$_1$–C$_3$alkoxy (preferably methoxy); R$^8$ is hydrogen, hydroxyethyl or methyl; R$^9$ is methyl, ethyl, isopropyl, trifluoromethyl or methoxyethyl; or triazolyl, imidazolyl or pyrazolyl.

More preferably still

R$^1$ is hydrogen;

R$^2$ and R$^3$, together with the interconnecting atoms, form a pyrrolidine ring;

Z is CF$_3$, OCF$_3$, SMe, or OMe;

Y is hydrogen, F, Cl, Br, methyl, ethyl, OMe or SMe; wherein at least one of Z or Y is para to the ether linkage linking ring A and ring B and is not hydrogen and the other Z or Y is meta to the ether linkage linking ring A and ring B; or when Z and Y are attached para and meta to the ether linkage linking rings A and B, Z and Y are linked so that, together with the interconnecting atoms, Z and Y form a fused 5 or 6-membered carbocyclic or heterocyclic ring wherein the linkages forming the fused ring are —(CH$_2$)$_3$—, —S(CH$_2$)$_2$—, —CH$_2$S—CH$_2$—, —SCH=N—, —(CH$_2$)$_4$—, —S(CH$_2$)$_2$O—, —N=CH=CH=CH—, —CH=N—CH=N— and —CH=CH—N=CH—, wherein either end of these linkages can be attached para to the ether linkage;

$R^4$ is hydrogen, and
$R^5$ is —$(CH_2)_p$—X, where p is 0 or 1; X is hydrogen, hydroxy, $CONR^6R^7$, $SO_2NR^6R^7$ or $NR^8SO_2R^9$; wherein $R^6$ and $R^7$, which may be the same or different, are hydrogen, $C_1$–$C_3$alkyl optionally substituted by hydroxy, —$CONH_2$ or $C_1$–$C_3$alkoxy (preferably methoxy); $R^8$ is hydrogen, hydroxyethyl or methyl; $R^9$ is methyl, ethyl, isopropyl, trifluoromethyl or methoxyethyl; or
triazolyl, imidazolyl or pyrazolyl.

More preferably still $R^4$ and $R^5$ are not both hydrogen.

Preferred compounds of formula (I) are:

(+) 4-[4-(methylsulfanyl)phenoxy]-3-(2-pyrrolidinyl) benzenesulfonamide hydrochloride;

N-methyl-4-[4-(methylsulfanyl)phenoxy]-3-(2-pyrrolidinyl)benzenesulfonamide;

N-methyl-N-{3-(2-pyrrolidinyl)-4-[4-(trifluoromethoxy) phenoxy]phenyl}-methanesulfonamide; and (+) N-{3-(2-pyrrolidinyl)-4-[4-(trifluoromethoxy)phenoxy] phenyl}-methanesulfonamide.

According to a second aspect, the invention provides a compound of general formula (I) or (IX):

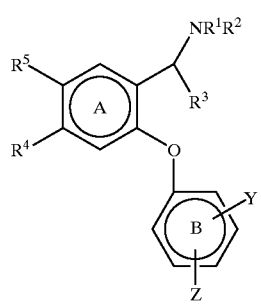

(I)

and pharmaceutically acceptable salts or solvates thereof wherein:

$R^1$ represents H or $C_1$–$C_6$ alkyl, $R^2$ and $R^3$, together with the nitrogen to which $R^2$ is attached and the carbon to which $R^3$ is attached, form a four to eight membered saturated ring containing one or two heteroatoms, including the nitrogen to which $R^2$ is attached, wherein a second heteroatom, if present, is selected from oxygen, nitrogen and sulfur, with the proviso that said ring cannot contain two adjacent heteroatoms;

Z is selected from the group including: $CF_3$, $OCF_3$, $SR^{12}$ or $C_1$–$C_4$ alkoxy and wherein $R^{12}$ represents $C_1$–$C_6$ alkyl; and Y is selected from the group including: hydrogen, halogen, —$OR^a$, $R^a$ or —$SR^{12}$, and wherein $R^a$ represents: $C_1$–$C_4$ alkyl (optionally substituted with fluorine atoms e.g. —$CF_3$);

or Z and Y when taken together can represent a fused 5 to 7 membered ring as illustrated by general formula IX, wherein said 5 to 7 membered ring may be saturated, unsaturated or aromatic, and wherein said 5 to 7 membered ring may optionally contain one or more heteroatoms P and Q, wherein P and Q=may be independently O, S or N, and wherein E, F, or G independently represent CH or $CH_2$ and wherein k and p may independently be=0, 1, 2 or 3, and m=1,2 or 3; and

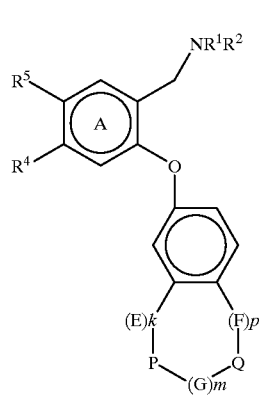

(IX)

$R^4$ and $R^5$ independently represent A—X wherein A=—$(CH_2)_n$—, wherein n represents 0, 1 or 2 and wherein X represents: H, F, Cl, Br, I, $CONR^6R^7$ or $SO_2NR^6R^7$, OH, $NR^8SO_2R^9$, $NO_2$, $NR^6R^{11}$, CN, $CO_2R^{10}$, CHO, $S(O)_mR^{10}$ wherein m=0, 1 or 2 and wherein $R^6$, $R^7$, $R^8$ and $R^{10}$ independently represent H or $C_{1-6}$ alkyl, wherein $R^9$ represents $C_{1-6}$ alkyl, $R^{11}$ represents H, $C_{1-6}$ alkyl, C(O) $R^6$, $CO_2R^9$; C(O)$NHR^6$ or $SO_2NR^6R^6$ and wherein said $C_{1-6}$ alkyl group is optionally substituted by one or more groups selected from OH, $CO_2H$, $C_{3-6}$ cycloalkyl, $NH_2$, $CONH_2$, $C_{1-6}$ alkoxy, $C_{1-6}$ alkoxycarbonyl and a 5- or 6-membered heterocyclic ring containing 1, 2 or 3 heteroatoms selected from N, S and O; or with the proviso that Z and Y together do not form a fused phenyl ring;

$R^4$ or $R^5$ may be representative of a 5- or 6-membered heterocyclic ring containing 1, 2 or 3 heteroatoms selected from N, S and O; and in addition, $R^6$ and $R^7$ may, together with the N atom to which they are attached, represent a 5- or 6-membered heterocyclic ring which may be optionally substituted; and pharmaceutically acceptable salts or solvates thereof with the proviso that both $R^4$ and $R^5$ are not H.

For the avoidance of doubt, unless otherwise indicated, the term substituted means substituted by one or more defined groups. In the case where groups may be selected from a number of alternatives groups, the selected groups may be the same or different.

For the avoidance of doubt, the term independently means that where more than one substituent is selected from a number of possible substituents, those substituents may be the same or different.

The compounds of the invention have the advantage that they are selective inhibitors of the re-uptake of serotonin (SRIs) (and so are likely to have reduced side effects), they have a rapid onset of action (making them suitable for administration shortly before an effect is required), they have desirable potency and associated properties. Compounds that selectively inhibit the re-uptake of serotonin, but not noradrenaline or dopamine, are preferred.

We have found that compounds of formula I which possess these properties have a relatively polar group at $R^4/R^5$.

According to a third aspect, the invention provides a compound of general formula I and pharmaceutically acceptable salts thereof, wherein $R^1$, $R^2$, $R^3$, Z and Y are as defined in the first aspect; and $R^4$ and $R^5$, which may be the same or different, are —(CH$_2$)$_p$—A', wherein p is 0, 1 or 2 and A' is a polar group. In this aspect, polar groups may be defined as those having a negative π-value according to the formula:

$$\pi_X = \log P_X - \log P_H$$

wherein log P$_X$ is the partition coefficient of a derivative and P$_H$ is that of the parent compound as further described in C. Hansch and A. Leo, 'Substitutent Constants for Correlation Analysis in Chemistry and Biology', Wiley, N.Y., 1979. In this system, H has a π-value of 0.00, —OCH$_3$ has a π-value of −0.02, and —SO$_2$NH$_2$ has a π-value of −1.82, for example [see Table VI-I, 'Well-Characterized Aromatic Substituents', p 49, ibid]. More preferred polar groups have a more negative π-value: thus, preferred groups have π-values of a greater negative value than −0.1, more preferably a greater negative value than −0.5, and most preferably a greater negative value than −1.0. Even when p is other than zero in the above definition, the definition of A' is based on the above reference as if p was zero.

The pharmaceutically or veterinarily acceptable salts of the compounds of formula I which contain a basic centre are, for example, non-toxic acid addition salts formed with inorganic acids such as hydrochloric, hydrobromic, hydroiodic, sulfuric and phosphoric acid, with carboxylic acids or with organo-sulfonic acids. Examples include the HCl, HBr, Hl, sulfate or bisulfate, nitrate, phosphate or hydrogen phosphate, acetate, benzoate, succinate, saccharate, fumarate, maleate, lactate, citrate, tartrate, gluconate, camsylate, methanesulfonate, ethanesulfonate, benzenesulfonate, p-toluenesulfonate and pamoate salts. Compounds of the invention can also provide pharmaceutically or veterinarily acceptable metal salts, in particular non-toxic alkali and alkaline earth metal salts, with bases. Examples include the sodium, potassium, aluminium, calcium, magnesium, zinc, diolamine, olamine, ethylenediamine, tromethamine, chloine, megulamine and diethanolamine salts. For reviews on suitable pharmaceutical salts see Berge et al, J. Pharm, Sci., 66, 1–19,1977; P L Gould, International Journal of Pharmaceutics, 33 (1986), 201–217; and Bighley et al, Encyclopedia of Pharmaceutical Technology, Marcel Dekker Inc, New York 1996, Volume 13, page 453–497.

The pharmaceutically acceptable solvates of the compounds of the invention include the hydrates thereof.

Also included within the scope of the compound and various salts of the invention are polymorphs thereof.

Hereinafter, compounds their pharmaceutically acceptable salts, their solvates or polymorphs, defined in any aspect of the invention (except intermediate compounds in chemical processes) are referred to as "compounds of the invention".

The compounds of the invention may possess one or more chiral centres and so exist in a number of stereoisomeric forms. All stereoisomers and mixtures thereof are included in the scope of the present invention. Racemic compounds may either be separated using preparative HPLC and a column with a chiral stationary phase or resolved to yield individual enantiomers utilising methods known to those skilled in the art. In addition, chiral intermediate compounds may be resolved and used to prepare chiral compounds of the invention.

The compounds of the invention may exist in one or more tautomeric forms. All tautomers and mixtures thereof are included in the scope of the present invention. For example, a claim to 2-hydroxypyridinyl would also cover its tautomeric form, α-pyridonyl.

The invention also includes radiolabelled compounds.

It will be appreciated by those skilled in the art that certain protected derivatives of compounds of the invention, which may be made prior to a final deprotection stage, may not possess pharmacological activity as such, but may, in certain instances, be administered orally or parenterally and thereafter metabolised in the body to form compounds of the invention which are pharmacologically active. Such derivatives may therefore be described as "prodrugs". Further, certain compounds of the invention may act as prodrugs of other compounds of the invention.

All protected derivatives and prodrugs of compounds of the invention are included within the scope of the invention. Examples of suitable pro-drugs for the compounds of the present invention are described in Drugs of Today, Volume 19, Number 9, 1983, pp 499–538 and in Topics in Chemistry, Chapter 31, pp 306–316 and in "Design of Prodrugs" by H. Bundgaard, Elsevier, 1985, Chapter 1 (the disclosures in which documents are incorporated herein by reference).

It will further be appreciated by those skilled in the art, that certain moieties, known to those skilled in the art as "pro-moieties", for example as described by H. Bundgaard in "Design of Prodrugs" (the disclosure in which document is incorporated herein by reference) may be placed on appropriate functionalities when such functionalities are present within compounds of the invention.

Preferred prodrugs for compounds of the invention include: esters, carbonate esters, hemi-esters, phosphate esters, nitro esters, sulfate esters, sulfoxides, amides, carbamates, azo-compounds, phosphamides, glycosides, ethers, acetals and ketals.

Compounds of the invention may be prepared, in known manner in a variety of ways. In the following reaction schemes and hereafter, unless otherwise stated, R$^1$ to R$^{13}$, Z and Y are as defined in the first aspect. These processes form further aspects of the invention.

Throughout the specification, general formulae are designated by Roman numerals I, II, III, IV etc. Subsets of these general formulae are defined as Ia, Ib, Ic etc, . . . IVa, IVb, IVc etc.

Compounds of formula (Ia), i.e. compounds of general formula I where R$^2$ and R$^3$ form a pyrrolidine ring, may be prepared from compounds of formula (II) by reaction with a hydride reducing agent in a suitable solvent (see Scheme 1). Suitable solvents include protic solvents such as ethanol. Sodium borohydride is an appropriate reducing agent as exemplified by Example 1 herein.

SCHEME 1

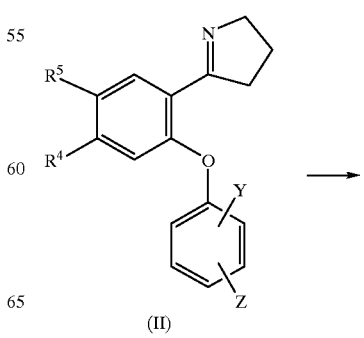

(II)

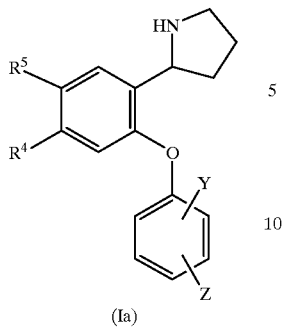

(Ia)

Compounds of general formula (II) may be prepared from compounds of formula (III) by treatment with acid in a suitable solvent under appropriate reaction conditions (see Scheme 2). Suitable solvents include 1,4-dioxane and suitable conditions are at elevated temperature as exemplified by Preparation 29 herein.

SCHEME 2

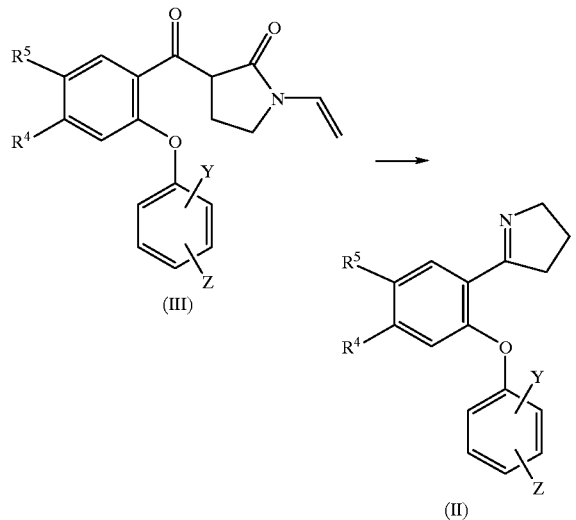

Compounds of general formula (III) may be prepared from compounds of formula (IV) by reaction with the anion of 1-vinyl-2-pyrrolidinone (formed by treatment with an appropriate base) under suitable reaction conditions (see Scheme 3). Lithium hexamethyldisilazide is a suitable base and suitable conditions are under an inert atmosphere at reduced temperature, preferably below −20° C. as exemplified by preparation 23 herein.

SCHEME 3

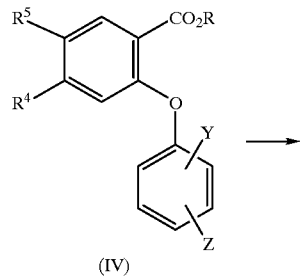

(IV)

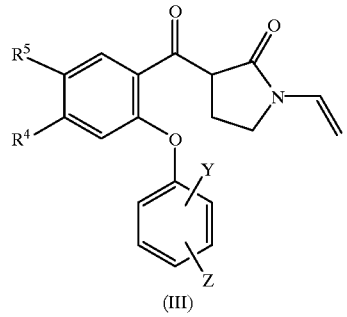

(III)

Compounds of general formula (IV) may be prepared from compounds of formula (V), where T is a group which can be converted to the group —$CO_2R$.

SCHEME 4

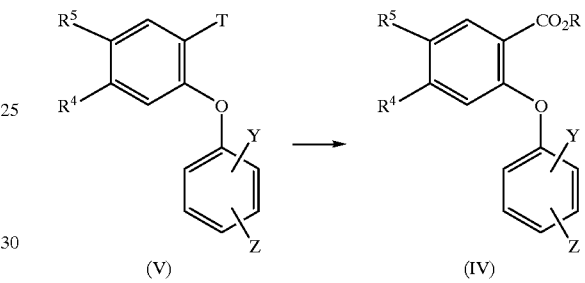

(V)        (IV)

i) When T is a halogen such as chloro, bromo or iodo, it may be converted to —$CO_2R$ by treatment with carbon monoxide at high pressure with a Pd(0) or (II) catalyst, in an alcohol solvent (ROH wherein R is $C_1$–$C_4$ alkyl), in the presence of a base at elevated temperatures. For example the reaction may be carried out at pressures in the region of about 60 p.s.i, whilst suitable Pd catalysts include palladium tetrakis(triphenylphosphine), suitable bases include triethylamine and suitable alcohol solvents include ethanol as exemplified by Preparation 21 herein.

ii) When T is a nitrile —CN, it may be converted to —$CO_2R$ by treatment with an acid in an alcohol solvent (ROH wherein R is $C_1$–$C_4$ alkyl) at elevated temperature. Alternatively a nitrile may be converted to —$CO_2R$ in two steps by first treating with a suitable hydroxide salt in the presence of water and a suitable co-solvent at elevated temperature to form compounds where T is —$CO_2H$. Suitable hydroxide salts include sodium hydroxide and suitable co-solvents include ethanol, as exemplified by Preparation 7 herein. The group —$CO_2H$ may be converted to —$CO_2R$ by treatment with an acid in an alcohol solvent (ROH wherein R is $C_1$–$C_4$ alkyl) at elevated temperature. Suitable acids include concentrated sulfuric acid and appropriate alcohol solvents include ethanol as exemplified by Preparation 11 herein.

Compounds of formula (V) may be prepared in turn from the coupling of compounds of general formula (VI) with compounds of general formula (VII), wherein L is a suitable leaving group such as halogen (F, Cl, Br or I) or a sulfonate ester such as trifluoromethanesulfonate or methanesulfonate, preferably L is F or Cl (see Scheme 5). Such coupling reaction may be accomplished by techniques known in the art, such as via reaction with potassium carbonate in a suitable solvent such as dimethylformamide under appropriate reaction conditions such as elevated temperature and in an inert atmosphere.

SCHEME 5

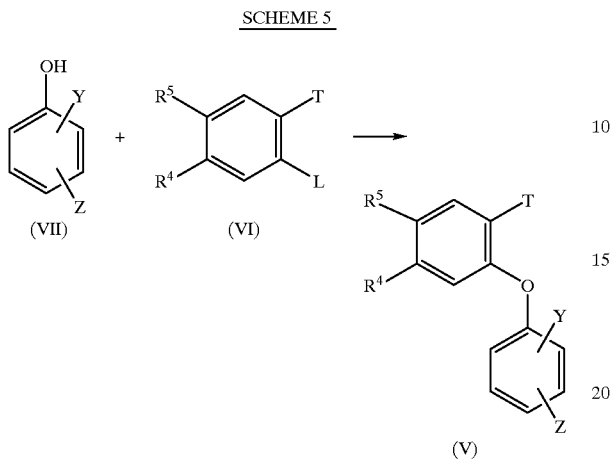

Alternatively, $R^4$ and/or $R^5$ may be introduced after formation of the amine containing ring (see Scheme 6). Compounds of general formula (Ib) may be prepared from compounds of general formula (Ic), i.e. compounds of general formula (Ib) where $R^4$ and $R^5$ are hydrogen. Compounds of general formula (Ic) may be prepared from (IVa) in an analogous fashion to the preparation of (Ia) from (IV) (see Scheme 1), while compounds of general formula (IVa) may be prepared from (VII) and (VIa) in an analogous fashion to the preparation of (IV) (see Scheme 1).

SCHEME 6

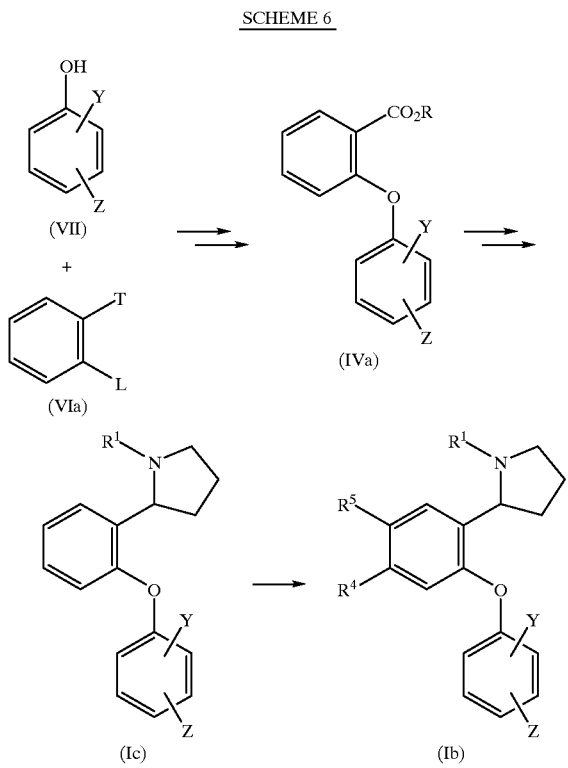

Methodologies for introducing $R^4$ and/or $R^5$ into compounds of formula (Ic) include:

i) Where $R^4/R^5$ are halogen, by reaction of (Ic) with a suitable halogenating agent in an inert solvent which does not adversely affect the reaction. Suitable halogenating agents include trifluoromethanesulfonic acid and N-iodosuccinimide and suitable inert solvents include dichloromethane.

ii) Where $R^4/R^5$ are —$NO_2$, by reaction of (Ic) with a suitable nitrating agent, such as an alkali metal nitrate, in an inert solvent which does not adversely affect the reaction at, or below, room temperature. Suitable nitrating agents include trifluoromethanesulfonic acid/ potassium nitrate and suitable inert solvents include trifluoroacetic acid as exemplified by Example 16 herein.

iii) Where $R^4/R^5$ is —$SO_2NR^6R^7$ by reaction of an intermediate sulfonyl chloride with the requisite amine of formula $HNR^6R^7$ in a suitable solvent. Suitable solvents include water and the reactions are generally performed at or below room temperature. The intermediate sulfonyl chlorides may be prepared from the amines (Ic) by reaction with chlorosulfonic acid under low temperature conditions and in the presence of an inert solvent which does not adversely affect the reaction. Suitable inert solvents include dichloromethane and a typical reaction temperature is 0° C., as illustrated by Examples 6 and 7 herein.

Alternatively, compounds of general formula (I) having a particular $R^4/R^5$ substituent may be converted into other compounds of formula (I) using known techniques. For example:

i) When $R^4/R^5$ is nitro, it may be reduced to the corresponding —$NH_2$ group via treatment with a reducing agent in a protic solvent at, or above, room temperature. Suitable reducing agents include iron powder/calcium chloride, suitable protic solvents include aqueous ethanol and at a typical reaction temperature of from about 70° C. to about 100° C., preferably about 90° C., as exemplified by Preparation 15 herein.

ii) When $R^4/R^5$ is —$NH_2$, it may be converted to the corresponding —$NHSO_2R^9$ group by reaction with a sulfonylating agent in the presence of a base in an inert solvent which does not adversely affect the reaction at, or below, room temperature. Suitable sulfonylating agents include methanesulfonyl chloride, suitable bases include triethylamine and suitable inert solvents include dichloromethane as exemplified by Preparations 40 and 41 herein.

iii) When $R^4/R^5$ is a —$NHSO_2R^9$ group, it may be converted to the corresponding —$NR^8SO_2R$ group via treatment with an alkylating agent and a base in a suitable inert solvent. Examples of suitable alkylating agents include methyl iodide, suitable bases include potassium carbonate and suitable inert solvents include acetonitrile, as exemplified by Preparation 43 herein.

Compounds of general formula (I) having a particular $R^1$ group may be converted into other compounds of formula (I) having a different $R^1$ group.

For example, compounds of formula (I) wherein $R^1$ is hydrogen, can be converted into compounds of formula (I) wherein $R^1$ is alkyl, by reaction with an aldehyde and a hydride reducing agent. For example, compounds wherein $R^1$ is methyl may be prepared in one step wherein the aldehyde is formaldehyde and suitable reducing agents include sodium triacetoxyborohydride. The reaction is preferably conducted in a solvent which does not interfere with the reaction, such as dichloromethane at or below room temperature, as exemplified by Example 12 herein. Alternatively the reaction may be conducted in two steps by reaction with a formylating agent in a suitable solvent, followed by subsequent reduction of the intermediate N-formyl compound with a hydride reducing agent in an inert solvent, preferably at elevated temperature. Suitable formylating agents include pentafluorophenyl formate (formed from formic acid, pentafluorophenol and dicyclohexylcarbodiimide) and suitable solvents for the formylation include dichloromethane as exemplified by Preparation 44 herein. Suitable reducing agents include borane-tetrahydrofuran complex and suitable inert solvents for the reduction include tetrahydrofuran as exemplified by Example 13 herein.

Compounds of general formula (VI) may be prepared in turn from compounds of general formula (VIII) (see Scheme 7). Compounds of formula (VI) may be prepared by aromatic electrophilic substitution of compounds of formula (VIII) to give compounds of formula (VI) directly. Alternatively compounds of formula (VI) may be prepared in two or more steps; aromatic electrophilic substitution of compounds of formula (VIII) to give intermediate compounds which then undergo further reaction to give compounds of formula (VI). The intermediate compounds may be isolated or generated in situ without isolation.

SCHEME 7

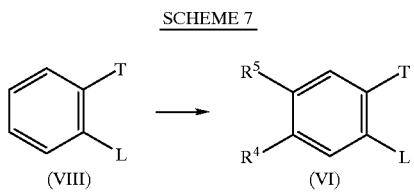

According to further aspects, the invention provides compounds of formulae II, III, IV and V as defined above.

Compounds of formulae VI, VII and VIII are either known and available from commercial sources or are available from commercially available materials using known techniques (see Examples hereinafter).

It will be apparent to those skilled in the art that sensitive functional groups may need to be protected and deprotected during synthesis of a compound of formula I. This may be achieved by conventional techniques, for example as described in 'Protective Groups in Organic Synthesis', 3rd edition, by T W Greene and P G M Wuts, John Wiley and Sons Inc, 1999. Example 18 provides one example of a protecting group strategy employed in the synthesis of a compound of the present invention.

The skilled chemist will appreciate that diaryl ethers may be prepared using a number of synthetic methodologies. For a review of methodologies see J S Sawyer, *Tetrahedron*, 56 (2000) 5045–5065, incorporated herein by reference.

The compounds of the invention are useful because they have pharmacological activity in mammals, including humans. More particularly, they are useful in the treatment or prevention of a disorder in which the regulation of monoamine transporter function is implicated. Disease states that may be mentioned include hypertension, depression (e.g. depression in cancer patients, depression in Parkinson's patients, postmyocardial infarction depression, subsyndromal symptomatic depression, depression in infertile women, paediatric depression, major depression, single episode depression, recurrent depression, child abuse induced depression, post partum depression and grumpy old man syndrome), generalized anxiety disorder, phobias (e.g. agoraphobia, social phobia and simple phobias), posttraumatic stress syndrome, avoidant personality disorder, premature ejaculation, eating disorders (e.g. anorexia nervosa and bulimia nervosa), obesity, chemical dependencies (e.g. addictions to alcohol, cocaine, heroin, phenobarbital, nicotine and benzodiazepines), cluster headache, migraine, pain, Alzheimer's disease, obsessive-compulsive disorder, panic disorder, memory disorders (e.g. dementia, amnestic disorders, and age-related cognitive decline (ARCD)), Parkinson's diseases (e.g. dementia in Parkinson's disease, neuroleptic-induced parkinsonism and tardive dyskinesias), endocrine disorders (e.g. hyperprolactinaemia), vasospasm (particularly in the cerebral vasculature), cerebellar ataxia, gastrointestinal tract disorders (involving changes in motility and secretion), negative symptoms of schizophrenia, premenstrual syndrome, fibromyalgia syndrome, stress incontinence, Tourette's syndrome, trichotillomania, kleptomania, male impotence, attention deficit hyperactivity disorder (ADHD), chronic paroxysmal hemicrania, headache (associated with vascular disorders), emotional lability, pathological crying, sleeping disorder (cataplexy) and shock.

Disorders of particular interest include depression, attention deficit hyperactivity disorder, obsessive-compulsive disorder, post-traumatic stress disorder, substance abuse disorders and sexual dysfunction including (in particular) premature ejaculation. Premature ejaculation may be defined as persistent or recurrent ejaculation before, upon or shortly after penile penetration of a sexual partner. It may also be defined as ejaculation occurring before the individual wishes [see 'The Merck Manual', 16$^{th}$ edition, p 1576, published by Merck Research Laboratories, 1992].

Thus, according to further aspects, the invention provides:
i) a compound of formula (I), as defined in the first aspect, or a pharmaceutically acceptable salt thereof, for use as a pharmaceutical;
ii) the use of a compound of formula (I), as defined in the first aspect, or a pharmaceutically acceptable salt thereof, in the manufacture of a medicament for the treatment or prevention of a disorder in which the regulation of monoamine transporter function is implicated, for example depression, attention deficit hyperactivity disorder, obsessive-compulsive disorder, post-traumatic stress disorder, substance abuse disorders or sexual dysfunction including premature ejaculation;
iii) the use of a compound of general formula (I) as defined in the first aspect, or a pharmaceutically acceptable salt thereof, in the manufacture of a medicament for the treatment or prevention of premature ejaculation, and also provides a method of treatment or prevention of premature ejaculation comprising the administration of this compound to a patient in need of such treatment or prevention;
iv) a method of treatment or prevention of depression, attention deficit hyperactivity disorder, obsessive-compulsive disorder, post-traumatic stress disorder, substance abuse disorders or sexual dysfunction including premature ejaculation, which comprises administering a therapeutically effective amount of a compound of formula (I), as defined in the first aspect, or a pharmaceutically acceptable salt thereof, to a patient in need of such treatment or prevention;
v) a method of increasing ejaculatory latency which comprises the administration of an effective amount of a compound of formula (I), as defined in the first aspect, or a pharmaceutically acceptable salt thereof, to a male desiring increased ejaculatory latency; and
vi) a compound of formula (I), as defined in the first aspect, or pharmaceutically acceptable salts, solvates or polymorphs thereof, for the treatment or prevention of a disorder in which the regulation of monoamine transporter function is implicated, for example depression, attention deficit hyperactivity disorder, obsessive-compulsive disorder, post-traumatic stress disorder, substance abuse disorders or sexual dysfunction including premature ejaculation.

It is to be appreciated that all references herein to treatment include curative, palliative and prophylactic treatment.

The compounds of the invention may be administered alone or as part of a combination therapy. If a combination of active agents are administered, then they may be administered simultaneously, separately or sequentially. In particular, the compounds of the invention may be combined with the following, preferably for the treatment of PE:

Alpha-blockers (e.g. phentolamine, doxazasim, tansulosin, terazasin, prazasin and Example 19 of WO9830560;

Apomorphine—teachings on the use of apomorphine as a pharmaceutical may be found in U.S. Pat. No. 5,945,117;

Dopamine D2 agonists (e.g. Premiprixal, Pharmacia Upjohn compound number PNU95666);

Melanocortin receptor agonists (e.g. Melanotan II);

PGE1 receptor agonists (e.g. alprostadil);

Mono amine transport inhibitors, particularly Noradrenaline Re-uptake Inhibitors (NRIs) (e.g. Reboxetine), other Serotonin Re-uptake Inhibitors (SRIs) (e.g. paroxetine) or Dopamine Re-uptake Inhibitors (DRIs);

5-HT3 antagonists (e.g. ondansetron and granisetron); and

PDE inhibitors such as PDE2 (e.g. erythro-9-(2-hydroxyl-3-nonyl)-adenine) and Example 100 of EP 0771799- incorporated herein by reference) and in particular a PDE5 inhibitor (e.g. sildenafil, 1-{[3-(3,4-dihydro-5-methyl-4-oxo-7-propylimidazo[5,1-f]-as-trazin-2-yl)-4-ethoxyphenyl]sulfonyl}-4-ethylpiperazine i.e. vardenafil/Bayer BA 38-9456 or IC351 (see structure below, Icos Lilly)).

IC351(Icos Lilly)

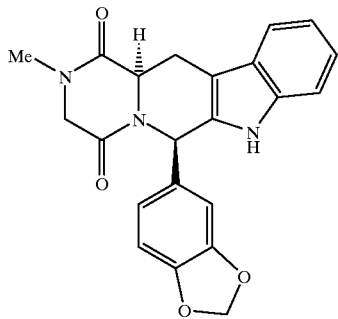

For human use the compounds of the invention can be administered alone but in human therapy will generally be administered in admixture with a suitable pharmaceutical excipient, diluent or carrier selected with regard to the intended route of administration and standard pharmaceutical practice.

For example, the compounds of the invention, can be administered orally, buccally or sublingually in the form of tablets, capsules (including soft gel capsules), ovules, elixirs, solutions or suspensions, which may contain flavouring or colouring agents, for immediate-, delayed-, modified-, sustained-, dual-, controlled-release or pulsatile delivery applications. The compounds of the invention may also be administered via intracavernosal injection. The compounds of the invention may also be administered via fast dispersing or fast dissolving dosage forms.

Such tablets may contain excipients such as microcrystalline cellulose, lactose, sodium citrate, calcium carbonate, dibasic calcium phosphate, glycine, and starch (preferably corn, potato or tapioca starch), disintegrants such as sodium starch glycollate, croscarmellose sodium and certain complex silicates, and granulation binders such as polyvinyl pyrrolidone, hydroxypropylmethylcellulose (HPMC), hydroxypropylcellulose (HPC), sucrose, gelatin and acacia. Additionally, lubricating agents such as magnesium stearate, stearic acid, glyceryl behenate and talc may be included.

Solid compositions of a similar type may also be employed as fillers in gelatin capsules, Preferred excipients in this regard include lactose, starch, a cellulose, milk sugar or high molecular weight polyethylene glycols. For aqueous suspensions and/or elixirs, the compounds of the invention, and their pharmaceutically acceptable salts, may be combined with various sweetening or flavouring agents, colouring matter or dyes, with emulsifying and/or suspending agents and with diluents such as water, ethanol, propylene glycol and glycerin, and combinations thereof.

Modified release and pulsatile release dosage forms may contain excipients such as those detailed for immediate release dosage forms together with additional excipients that act as release rate modifiers, these being coated on and/or included in the body of the device. Release rate modifiers include, but are not exclusively limited to, hydroxypropylmethyl cellulose, methyl cellulose, sodium carboxymethylcellulose, ethyl cellulose, cellulose acetate, polyethylene oxide, Xanthan gum, Carbomer, ammonio methacrylate copolymer, hydrogenated castor oil, carnauba wax, paraffin wax, cellulose acetate phthalate, hydroxypropylmethyl cellulose phthalate, methacrylic acid copolymer and mixtures thereof. Modified release and pulsatile release dosage forms may contain one or a combination of release rate modifying excipients. Release rate modifying excipients may be present both within the dosage form i.e. within the matrix, and/or on the dosage form, i.e. upon the surface or coating.

Fast dispersing or dissolving dosage formulations (FDDFs) may contain the following ingredients: aspartame, acesulfame potassium, citric acid, croscarmellose sodium, crospovidone, diascorbic acid, ethyl acrylate, ethyl cellulose, gelatin, hydroxypropylmethyl cellulose, magnesium stearate, mannitol, methyl methacrylate, mint flavouring, polyethylene glycol, fumed silica, silicon dioxide, sodium starch glycolate, sodium stearyl fumarate, sorbitol, xylitol. The terms dispersing or dissolving as used herein to describe FDDFs are dependent upon the solubility of the drug substance used i.e. where the drug substance is insoluble a fast dispersing dosage form can be prepared and where the drug substance is soluble a fast dissolving dosage form can be prepared.

The compounds of the invention can also be administered parenterally, for example, intravenously, intra-arterially, intraperitoneally, intrathecally, intraventricularly, intraurethrally, intrasternally, intracranially, intramuscularly or subcutaneously, or they may be administered by infusion techniques. For such parenteral administration they are best used in the form of a sterile aqueous solution which may contain other substances, for example, enough salts or glucose to make the solution isotonic with blood. The aqueous solutions should be suitably buffered (preferably to a pH of from 3 to 9), if necessary. The preparation of suitable parenteral formulations under sterile conditions is readily accomplished by standard pharmaceutical techniques well known to those skilled in the art.

For oral and parenteral administration to human patients, the daily dosage level of the compounds of the invention or salts or solvates thereof will usually be from 10 to 500 mg (in single or divided doses).

Thus, for example, tablets or capsules of the compounds of the invention or salts or solvates thereof may contain from 5 mg to 250 mg of active compound for administration singly or two or more at a time, as appropriate. The physician in any event will determine the actual dosage which will be most suitable for any individual patient and it will vary with the age, weight and response of the particular patient. The above dosages are exemplary of the average case. There can, of course, be individual instances where higher or lower dosage ranges are merited and such are within the scope of this invention. The skilled person will also appreciate that, in the treatment of certain conditions (including PE), compounds of the invention may be taken as a single dose on an "as required" basis (i.e. as needed or desired).

Example Tablet Formulation

In general a tablet formulation could typically contain between about 0.01 mg and 500 mg of a compound according to the present invention (or a salt thereof) whilst tablet fill weights may range from 50 mg to 1000 mg. An example formulation for a 10 mg tablet is illustrated:

| Ingredient | % w/w |
| --- | --- |
| Free acid, Free base or Salt of Compound | 10.000* |
| Lactose | 64.125 |
| Starch | 21.375 |
| Croscarmellose Sodium | 3.000 |
| Magnesium Stearate | 1.500 |

*This quantity is typically adjusted in accordance with drug activity.

The compounds of the invention can also be administered intranasally or by inhalation and are conveniently delivered in the form of a dry powder inhaler or an aerosol spray presentation from a pressurised container, pump, spray or nebulizer with the use of a suitable propellant, e.g. dichlorodifluoromethane, trichlorofluoromethane, dichlorotetra-fluoro-ethane, a hydrofluoroalkane such as 1,1,1,2-tetrafluoroethane (HFA 134A [trade mark]) or 1,1,1,2,3,3,3-heptafluoropropane (HFA 227EA [trade mark]), carbon dioxide or other suitable gas. In the case of a pressurised aerosol, the dosage unit may be determined by providing a valve to deliver a metered amount. The pressurised container, pump, spray or nebulizer may contain a solution or suspension of the active compound, e.g. using a mixture of ethanol and the propellant as the solvent, which may additionally contain a lubricant, e.g. sorbitan trioleate. Capsules and cartridges (made, for example, from gelatin) for use in an inhaler or insufflator may be formulated to contain a powder mix of a compound of the invention and a suitable powder base such as lactose or starch.

Aerosol or dry powder formulations are preferably arranged so that each metered dose or "puff" contains from 1 to 50 mg of a compound of the invention for delivery to the patient. The overall daily dose with an aerosol will be in the range of from 1 to 50 mg which may be administered in a single dose or, more usually, in divided doses throughout the day.

The compounds of the invention may also be formulated for delivery via an atomiser. Formulations for atomiser devices may contain the following ingredients as solubilisers, emulsifiers or suspending agents: water, ethanol, glycerol, propylene glycol, low molecular weight polyethylene glycols, sodium chloride, fluorocarbons, polyethylene glycol ethers, sorbitan trioleate, oleic acid.

Alternatively, the compounds of the invention can be administered in the form of a suppository or pessary, or they may be applied topically in the form of a gel, hydrogel, lotion, solution, cream, ointment or dusting powder. The compounds of the invention may also be dermally or transdermally administered, for example, by the use of a skin patch. They may also be administered by the ocular, pulmonary or rectal routes.

For ophthalmic use, the compounds can be formulated as micronized suspensions in isotonic, pH adjusted, sterile saline, or, preferably, as solutions in isotonic, pH adjusted, sterile saline, optionally in combination with a preservative such as a benzylalkonium chloride. Alternatively, they may be formulated in an ointment such as petrolatum.

For application topically to the skin, the compounds of the invention can be formulated as a suitable ointment containing the active compound suspended or dissolved in, for example, a mixture with one or more of the following: mineral oil, liquid petrolatum, white petrolatum, propylene glycol, polyoxyethylene polyoxypropylene compound, emulsifying wax and water. Alternatively, they can be formulated as a suitable lotion or cream, suspended or dissolved in, for example, a mixture of one or more of the following: mineral oil, sorbitan monostearate, a polyethylene glycol, liquid paraffin, polysorbate 60, cetyl esters, wax, cetearyl alcohol, 2-octyidodecanol, benzyl alcohol and water.

The compounds of the invention may also be used in combination with a cyclodextrin. Cyclodextrins are known to form inclusion and non-inclusion complexes with drug molecules. Formation of a drug-cyclodextrin complex may modify the solubility, dissolution rate, bioavailability and/or stability property of a drug molecule. Drug-cyclodextrin complexes are generally useful for most dosage forms and administration routes. As an alternative to direct complexation with the drug the cyclodextrin may be used as an auxiliary additive, e.g. as a carrier, diluent or solubiliser. Alpha-, beta- and gamma-cyclodextrins are most commonly used and suitable examples are described in WO-A-91/11172, WO-A-94/02518 and WO-A-98/55148.

For oral or parenteral administration to human patients the daily dosage levels of compounds of formula (I), and their pharmaceutically acceptable salts, will be from 0.01 to 30 mg/kg (in single or divided doses) and preferably will be in the range 0.01 to 5 mg/kg. Thus tablets will contain 1 mg to 0.4 g of compound for administration singly or two or more at a time, as appropriate. The physician will in any event determine the actual dosage which will be most suitable for any particular patient and it will vary with the age, weight and response of the particular patient. The above dosages are, of course only exemplary of the average case and there may be instances where higher or lower doses are merited, and such are within the scope of the invention.

Oral administration is preferred. Preferably, administration takes place shortly before an effect is required.

For veterinary use, a compound of the invention, or a veterinarily acceptable salt thereof, or a veterinarily acceptable solvate or pro-drug thereof, is administered as a suitably acceptable formulation in accordance with normal veterinary practice and the veterinary surgeon will determine the dosing regimen and route of administration which will be most appropriate for a particular animal.

EXAMPLE 1

2-{2-[4-(Methylsulfanyl)phenoxy]phenyl}pyrrolidine hydrochloride

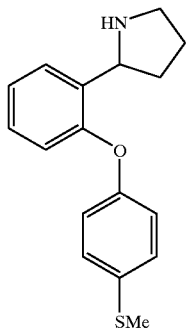

Sodium borohydride (6.09 g, 161 mmol) was added to a solution of the imine of Preparation 29 (33.04 g) in EtOH (270 mL) and the mixture was stirred at room temperature under nitrogen for 3.5 days. 2M HCl (40 mL) was added dropwise, resulting in a thick yellow slurry. After 10 min a further portion of 2M HCl (40 mL) was added and after another 10 min a final portion of 2M HCl (80 mL). After stirring for 40 min the mixture was basified by the addition of 6M NaOH and extracted with ether (1 L). The organic layer was washed with brine (500 mL), dried (MgSO$_4$) and evaporated to give a brown oil. The oil was taken up in 10% EtOH in ether (350 mL) and 1 M ethereal HCl (150 mL) was added dropwise with stirring. The resulting precipitate of the hydrochloride salt was collected by filtration and then dried in vacuo at 50° C. to give a light brown solid (18.54 g, 72%); $\delta_H$ (CD$_3$OD, 400 MHz) 2.05–2.19 (1H, m), 2.20–2.40 (2H, m), 2.45 (3H, s), 3.40 (2H, m), 4.93 (1H, t), 6.80 (1H, d), 7.05 (2H, d), 7.19 (1H, t), 7.37 (3H, m), 7.53 (1H, d); MS m/z (TS$^+$) 286 (MH$^+$).

EXAMPLES 2 TO 5

The examples below were prepared in analogous fashion to Example 1 by reduction of the appropriate imine precursor with sodium borohydride.

Thus according to a further aspect, the invention provides a pharmaceutical formulation containing a compound of formula (I), as defined in the first aspect, or a pharmaceutically acceptable salt thereof, and a pharmaceutically acceptable adjuvant, diluent or carrier.

The invention is illustrated by the following non-limiting Examples in which the following abbreviations and definitions are used:

| | |
|---|---|
| br | broad |
| Celite ® | filter agent, from Aldrich Chemical Company |
| δ | chemical shift |
| d | doublet |
| Δ | heat |
| DCM | dichloromethane |
| DMF | N,N-dimethylformamide |
| DMSO | dimethylsulfoxide |
| ES$^-$ | electrospray ionisation negative scan |
| ES$^+$ | electrospray ionisation positive scan |
| h | hours |
| HMDS | hexamethyldisilazide |
| IPA | isopropyl alcohol |
| m/z | mass spectrum peak |
| min | minutes |
| MS | mass spectrum |
| q | quartet |
| s | singlet |
| t | triplet |
| TFA | trifluoroacetic acid |
| TFAA | trifluoroacetic anhydride |
| THF | tetrahydrofuran |
| TLC | thin layer chromatography |
| TS$^+$ | thermospray ionisation positive scan |

Where indicated, compounds were characterised as their hydrochloride salts. A typical procedure for formation of hydrochloride salts is given in Example 1. The procedure can be carried out with other solvents e.g. diethyl ether, EtOAc or DCM.

| Ex | Prep | R$^5$ | Z | data |
|---|---|---|---|---|
| 2 | Prep 30 | H | 4-CF$_3$-phenyl | HCl salt: $\delta_H$ (CD$_3$OD, 400 MHz) 2.16 (1H, m), 2.23–2.38 (2H, m), 2.48 (1H, m), 3.41–3.50 (2H, m), 4.91 (1H, m), 7.00 (1H, d), 7.25 (2H, d), 7.32 (1H, t), 7.47 (1H, t), 7.63 (1H, d), 7.75 (2H, d); MS m/z (ES$^+$) 308 (MH$^+$) |

| Ex | Prep | R⁵ | Z | data |
|---|---|---|---|---|
| 3 | Prep 31 | H | 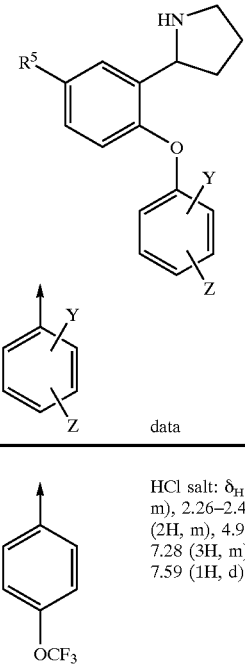 (4-OCF₃ phenyl) | HCl salt: δ_H (CD₃OD, 400 MHz) 2.18 (1H, m), 2.26–2.42 (2H, m), 2.48 (1H, m), 3.45 (2H, m), 4.95 (1H, m), 6.90 (1H, d), 7.19–7.28 (3H, m), 7.37 (2H, d), 7.43 (1H, m), 7.59 (1H, d); MS m/z (TS⁺) 324 (MH⁺) |
| 4 | Prep 32 | Br | 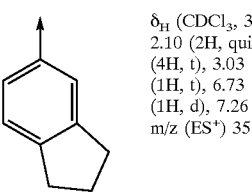 (indanyl) | δ_H (CDCl₃, 300 MHz) 1.60–2.00 (3H, m), 2.10 (2H, quintet), 2.24 (1H, m), 2.87 (4H, t), 3.03 (1H, m), 3.19 (1H, m), 4.43 (1H, t), 6.73 (2H, m), 6.82 (1H, s), 7.17 (1H, d), 7.26 (1H, dd), 7.74 (1H, d); MS m/z (ES⁺) 358, 360 (MH⁺) |
| 5 | Prep 34 | —NHSO₂Me | 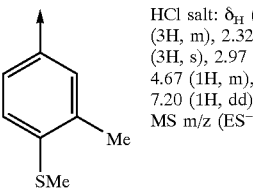 (3-Me-4-SMe phenyl) | HCl salt: δ_H (CD₃OD, 400 MHz) 1.99–2.19 (3H, m), 2.32 (3H, s), 2.37 (1H, m), 2.44 (3H, s), 2.97 (3H, s), 3.20–3.33 (2H, m), 4.67 (1H, m), 6.83 (1H, d), 6.90 (2H, m), 7.20 (1H, dd), 7.27 (1H, d), 7.41 (1H, d); MS m/z (ES⁻) 391 (M-H⁺) |

EXAMPLES 6 AND 7

(−)4-[4-(Methylsulfanyl)phenoxy]-3-(2-pyrrolidinyl)benzenesulfonamide hydrochloride (Example 6) and (+)4-[4-(Methylsulfanyl)phenoxy]-3-(2-pyrrolidinyl)benzenesulfonamide hydrochloride (Example 7)

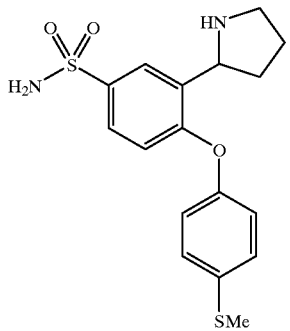

Chlorosulfonic acid (8.23 mL, 83 mmol) was added cautiously to a solution of the amide of Preparation 35 (8.3 mmol) in DCM (33 mL) and the mixture was stirred for 2 h before being poured into ice-water and extracted with DCM (1 L). This solution of crude intermediate sulfonyl chloride was dried (MgSO₄) and evaporated then dissolved in THF (40 mL) and treated with a mixture of conc. NH₃ (aq) (8.3 mL) and water (8.3 mL). The mixture was stirred at room temperature for 16 h then evaporated to dryness. The residue was dissolved in ethanol (50 mL) and 1 M LiOH (100 mL) was added. The mixture was stirred at room temperature for 3 h, the organic solvent was removed in vacuo and the mixture was diluted with water (200 mL) and extracted with EtOAc (500 mL). The organic layer was dried (MgSO₄) and evaporated. Purification by column chromatography [SiO₂; EtOAc increasing polarity to 5% (1:9 NH₄OH:MeOH) in EtOAc] gave the desired product as a light brown oil. This was taken up EtOAc and 1 M ethereal HCl was added to precipitate the hydrochloride salt. The precipitate was collected and dried to give a white solid (488 mg, 15%); δ_H(CD₃OD, 400 MHz) 2.13–2.60 (7H, m), 3.40–3.55 (2H, m), 5.03 (1H, m), 6.91 (1H, d), 7.18 (2H, d), 7.41 (2H, d), 7.90 (1H, d), 8.05 (1H, s); MS m/z (ES⁺) 365 (MH⁺). The enantiomers were separated on a Chiracel® OD250 chiral column using hexane/IPA/diethylamine as an eluent and then converted to their HCl salts to give Example 6 ($[\alpha]_D^{25}$=−27.8, c=0.1 MeOH) and Example 7 $[\alpha]_D^{25}$=+24.2, c=0.1 MeOH).

EXAMPLES 8–11

The following sulfonamides were prepared in an analogous fashion to that described herein for Examples 6 and 7, replacing ammonia with the required amine where appropriate. Where indicated the racemic products were separated by chiral HPLC.

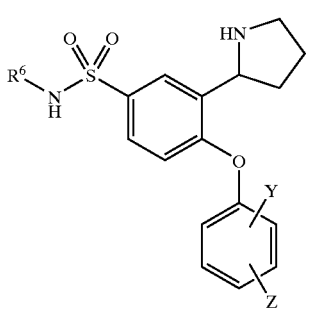

| Ex | Prep | R⁶ |  | data |
|---|---|---|---|---|
| 8 | Prep 36 | H | 4-CF₃-C₆H₄ | $\delta_H$ (CDCl₃, 400 MHz) 1.67 (1H, m), 1.79–1.99 (2H, m), 2.29 (1H, m), 3.07 (1H, m), 3.17 (1H, m), 2.90–3.20 (3H, br), 4.52 (1H, t), 6.90 (1H, d), 7.08 (2H, d), 7.63 (2H, d), 7.77 (1H, dd), 8.27 (1H, d); MS m/z (ES⁺) 387 (MH⁺) |
| 9 | Prep 36 | Me | 4-CF₃-C₆H₄ | HCl salt: $\delta_H$ (DMSO-d₆, 400 MHz) 2.03 (1H, m), 2.12–2.25 (2H, m), 2.43 (1H, m), 2.47 (3H, d), 3.40 (2H, obscured), 4.92 (1H, m), 7.10 (1H, d), 7.45 (2H, d), 7.58 (1H, m), 7.82 (1H, dd), 7.91 (2H, d), 8.07 (1H, d), 9.24 (1H, br), 9.96 (1H, br); MS m/z (ES⁺) 401 (MH⁺) |
| 10ᵃ | Prep 35 | Me | 4-SMe-C₆H₄ | $[\alpha]_D^{25}$ = +20.4, c = 0.1 MeOH; $\delta_H$ (CD₃OD, 400 MHz) 2.08–2.45 (4H, m), 2.48 (3H, s), 2.51 (3H, s), 3.36–3.50 (2H, m), 5.00 (1H, m), 6.90 (1H, d), 7.12 (2H, d), 7.38 (2H, d), 7.79 (2H, d), 7.94 (1H, s); MS m/z (ES⁺) 329 (MH⁺) |
| 11ᵃ,ᵇ | Prep 35 | Me | 4-SMe-C₆H₄ | $[\alpha]_D^{25}$ = −16.2, c = 0.1 MeOH; $\delta_H$ (CD₃OD, 400 MHz) 2.08–2.45 (4H, m), 2.48 (3H, s), 2.51 (3H, s), 3.36–3.50 (2H, m), 5.00 (1H, m), 6.90 (1H, d), 7.12 (2H, d), 7.38 (2H, d), 7.79 (2H, d), 7.94 (1H, s); MS m/z (ES⁺) 329 (MH⁺) |

ᵃThe enantiomers were separated on a Chiralpak® chiral column using hexane/IPA/diethylamine as an eluent
ᵇ93% enantiomeric excess

EXAMPLE 12

1-Methyl-2-{2-[4-(methylsulfanyl)phenoxy]phenyl}pyrrolidine hydrochloride

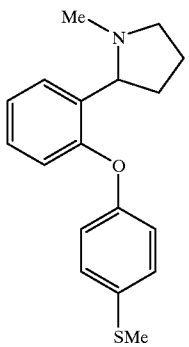

Formaldehyde (37% aq soln, 4.73 mL, 60 mmol) was added to a suspension of the product from Example 1 (6.44 g, 20 mmol) in DCM (100 mL) followed by Et$_3$N (5.58 mL, 40 mmol) and then NaHB(OAc)$_3$ (16.96 g, 80 mmol). The mixture was stirred at room temperature for 4 days then quenched by the addition of 2M HCl (80 mL). After stirring for 1 h the mixture was basified by the addition of saturated K$_2$CO$_3$ (aq). The mixture was extracted with DCM and the organic extract was dried (MgSO$_4$) and evaporated to give a brown oil (5.92 g, 99%). A sample was converted to the hydrochloride salt by addition of ethereal HCl to a solution in DCM; $\delta_H$ (CD$_3$OD, 400 MHz) 2.10–2.45 (3H, m), 2.48 (3H, s), 2.56 (1H, m), 2.90 (3H, s), 3.38 (1H, m), 3.84 (1H, m), 4.80 (1H, m), 6.92 (1H, d), 7.06 (2H, d), 7.23 (1H, t), 7.37 (2H, d), 7.43 (1H, t), 7.62 (1H, d); MS m/z (TS$^+$) 300 (MH$^+$).

EXAMPLE 13

(+) 3-(1-Methyl-2-pyrrolidinyl)-4-[4-(methylsulfanyl)phenoxy]benzenesulfonamide hydrochloride

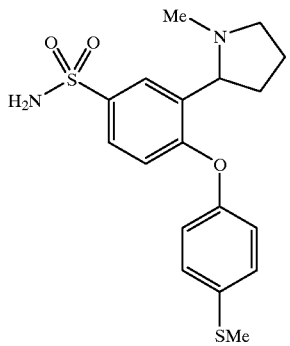

A solution of BH$_3$.THF in THF (1M, 1 mL, 1 mmol) was added to a solution of the amide of Preparation 44 (0.22 mmol) in THF (1 mL) and the mixture was heated at reflux for 1.5 h under N$_2$. After cooling to room temperature the reaction was quenched by the cautious addition of MeOH (10 mL). 2M HCl (20 mL) was then added and the mixture was heated at reflux for 30 min. After cooling to room temperature the mixture was diluted with water (20 mL) and basified with K$_2$CO$_3$. The mixture was concentrated to ~40 mL in vacuo and extracted with DCM (2×). The combined organic extracts were dried (MgSO$_4$) and evaporated to give an oil which was taken up in DCM and treated with 1M ethereal HCl. The mixture was concentrated in vacuo to give the product (68 mg, 75%) as white solid; ([α]$_D^{25}$=+9.2, c=0.14 MeOH); $\delta_H$ (CD$_3$OD, 400 MHz) 2.12–2.47 (3H, m), 2.50 (3H, s), 2.58–2.64 (1H, m), 2.94 (3H, s), 3.36 (1H, m), 3.88 (1H, m), 4.95 (1H, t), 6.98 (1H, d), 7.16 (2H, d), 7.40 (2H, d), 7.91 (1H, d), 8.18 (1H, s); MS m/z (ES$^+$) 379 (MH$^+$).

EXAMPLE 14

(−) 3-(1-Methyl-2-pyrrolidinyl)-4-[4-(methylsulfanyl)phenoxy]benzenesulfonamide hydrochloride

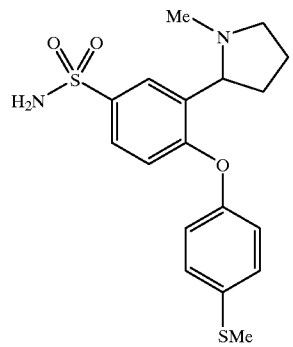

The title compound was prepared from the amide of Preparation 45 by the method of Example 13; ([α]$_D^{25}$=−8.0, c=0.16 MeOH); $\delta_H$ (CD$_3$OD, 400 MHz) 2.12–2.47 (3H, m), 2.50 (3H, s), 2.58–2.64 (1H, m), 2.94 (3H, s), 3.36 (1H, m), 3.88 (1H, m), 4.95 (1H, t), 6.98 (1H, d), 7.16 (2H, d), 7.40 (2H, d), 7.91 (1H, d), 8.18 (1H, s); MS m/z (ES$^+$) 379 (MH$^+$).

EXAMPLES 13 AND 14

Alternatively a racemic mixture of Examples 13 and 14 can be prepared as follows from the amine of Example 12.

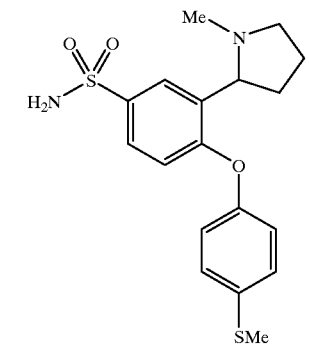

Chlorosulfonic acid (5.85 mL, 88 mmol) was added cautiously to a solution of the amine of Example 12 (2.635 g, 8.8 mmol) in DCM (35 mL) at 0° C. and the mixture was stirred at room temperature for 3 h before being poured into ice-water (350 mL) and extracted with DCM (500 mL). This solution of crude intermediate sulfonyl chloride was dried (MgSO$_4$) and evaporated then dissolved in THF (88 mL) and treated with a mixture of conc. NH$_3$ (aq) (8.8 mL) and water (8.8 mL). Mixture stirred at room temperature for 16 hrs then evaporated to dryness and partitioned between EtOAc (100 mL) and water (100 mL). The organic layer was dried (MgSO$_4$) and evaporated to give a brown oil. Purification by column chromatography [SiO$_2$; 2% (1:9 NH$_4$OH:MeOH) in DCM, increasing polarity to 6%] gave the product as a light brown oil. This was taken up in ether and 1M ethereal HCl was added to form the HCl salt. Solvent was removed in vacuo to give a white solid (1.105 g, 30%); δ$_H$ (CD$_3$OD, 400 MHz) 2.12–2.47 (3H, m), 2.50 (3H, s), 2.58–2.64 (1H, m), 2.94 (3H, s), 3.36 (1H, m), 3.88 (1H, m), 4.95 (1H, t), 6.98 (1H, d), 7.16 (2H, d), 7.40 (2H, d), 7.91 (1H, d), 8.18 (1H, s); MS m/z (TS$^+$) 379 (MH$^+$).

EXAMPLE 15

N-Methyl-3-(1-Methyl-2-pyrrolidinyl)-4-[4-(methylsulfanyl)phenoxy]-benzenesulfonamide hydrochloride This compound was synthesised by the same method as for Examples 13 and 14, from the amine of Example 12, except that 2M methylamine in THF was used in the final step in place of conc. NH$_3$ (aq). This gave a white solid (1.286 g, 34%); δ$_H$ (CD$_3$OD, 400 MHz) 2.12–2.46 (3H, m), 2.50 (3H, s), 2.57 (3H, s), 2.60–2.65 (1H, m), 2.86 (3H, s), 3.38 (1H, m), 3.88 (1H, m), 4.96 (1H, t), 7.00 (1H, d), 7.17 (2H, d), 7.40 (2H, d), 7.83 (1H, d), 8.09 (1H, s); MS m/z (TS$^+$) 393 (MH$^+$).

EXAMPLE 16

2-{5-Nitro-2-[4-(trifluoromethoxy)phenoxy]phenyl}pyrrolidine

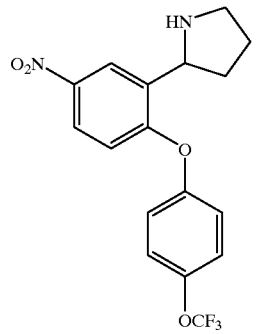

Triflic acid (4.88 mL, 55.5 mmol) was added dropwise to a solution of the amine of Example 3 hydrochloride salt (8.0 g, 22.2 mmol) in TFA (56 mL) at 0° C. and KNO$_3$ (2.36 g, 23.3 mmol) was then added portionwise over 15 min. The reaction was stirred at 0° C. for 3 h then poured into a 1:1 mixture of ice and 880 NH$_3$ (700 mL). The mixture was stirred for 30 min then extracted with EtOAc (1 L). The organic extract was dried (MgSO$_4$) and evaporated to give the product (11.44 g, assumed quantitative yield) as a red oil which was used without further purification; δ$_H$ (CD$_3$OD, 400 MHz) 1.90–2.14 (3H, m), 2.43 (1H, m), 3.19 (1H, m), 3.26 (1H, m), 4.70 (1H, t), 6.95 (1H, d), 7.26 (2H, d), 7.41 (2H, d), 8.18 (1H, dd), 8.48 (1H, d); MS m/z (ES$^+$) 369 (MH$^+$).

EXAMPLE 17

2-{5-Nitro-2-[4-(trifluoromethyl)phenoxy]phenyl}pyrrolidine

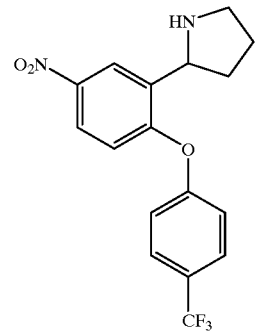

The reaction of Example 16 was repeated using the amine of Example 2 to give the title compound; δ$_H$ (CDCl$_3$, 400 MHz) 1.77–2.00 (3H, m), 2.33 (1H, m), 3.06–3.44 (1H, br), 3.15 (1H, m), 3.23 (1H, m), 4.63 (1H, t), 6.83 (1H, d), 7.14 (2H, d), 7.64 (2H, d), 8.06 (1H, dd), 8.52 (1H, d); MS m/z (TS$^+$) 353 (MH$^+$).

EXAMPLE 18

Trifluoro-N-{3-(2-pyrrolidinyl)-4-[4-(trifluoromethoxyphenoxy]phenyl}-methanesulfonamide hydrochloride

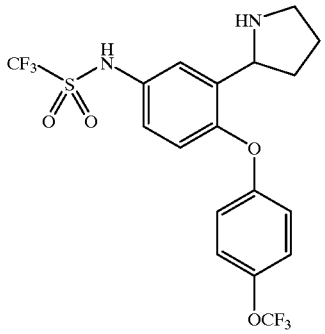

hydrogen chloride gas was bubbled through a solution of the sulfonamide of Preparation 39 (1.133 g, 1.99 mmol) in DCM (20 mL) at 0° C. for 15 min. The mixture was stirred at this temperature for 1 h then the solvent was removed in vacuo to give the product (1.008 g, 100%) as a pale purple solid; δ$_H$ (CD$_3$OD, 400 MHz) 2.12 (1H, m), 2.21–2.34 (2H, m), 2.47 (1H, m), 3.32–3.46 (2H, m), 4.90 (1H, m), 6.89 (1H, d), 7.21 (2H, d), 7.29 (1H, dd), 7.36 (2H, d), 7.47 (1H, d); MS m/z (ES$^+$) 471 (MH$^+$).

EXAMPLES 19–22

Examples 19–22 were prepared from the appropriate Boc protected precursors by the method of Example 18.

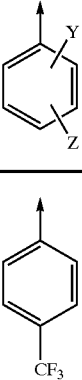

| Ex | Prep | R⁸ | Z | data |
|---|---|---|---|---|
| 19 | Prep 42 | H | 4-CF₃-phenyl | HCl salt: $\delta_H$ (CD₃OD, 400 MHz) 2.13 (1H, m), 2.28 (2H, m), 2.48 (1H, m), 2.99 (3H, s), 3.43 (2H, m), 4.87 (1H, obscured), 7.02 (1H, d), 7.25 (2H, d), 7.33 (1H, dd), 7.52 (1H, d), 7.74 (2H, d); MS m/z (TS⁺) 401 (MH⁺) |
| 20 | Prep 43 | Me | 4-OCF₃-phenyl | HCl salt: $\delta_H$ (CD₃OD, 400 MHz) 2.16 (1H, m), 2.23–2.41 (2H, m), 2.50 (1H, m), 2.93 (3H, s), 3.29 (3H, s), 3.39–3.49 (2H, m), 4.95 (1H, m), 6.92 (1H, d), 7.24 (2H, d), 7.39 (2H, d), 7.48 (1H, dd), 7.61 (1H, d); MS m/z (ES⁺) 431 (MH⁺) |
| 21ᵃ | Prep 40 | H | 4-OCF₃-phenyl | HCl salt: $[\alpha]_D^{25} = -19.5$, c = 0.2 MeOH); $\delta_H$ (CD₃OD, 400 MHz) 2.16 (1H, m), 2.29 (2H, m), 2.47 (1H, m), 2.99 (3H, s), 3.43 (2H, m), 4.92 (1H, t), 6.92 (1H, d), 7.19 (2H, d), 7.29 (1H, d), 7.37 (2H, d), 7.51 (1H, s); MS m/z (TS⁺) 417 (MH⁺) |
| 22ᵃ | Prep 41 | H | 4-OCF₃-phenyl | HCl salt: $[\alpha]_D^{25} = +18.9$, c = 0.2 MeOH); $\delta_H$ (CD₃OD, 400 MHz) 2.16 (1H, m), 2.29 (2H, m), 2.47 (1H, m), 2.99 (3H, s), 3.43 (2H, m), 4.92 (1H, t), 6.92 (1H, d), 7.19 (2H, d), 7.29 (1H, d), 7.37 (2H, d), 7.51 (1H, s); MS m/z (TS⁺) 417 (MH⁺) |

ᵃA racemic mixture of Examples 21 and 22 can also be prepared by the method of Example 1 from the imine of Preparation 33.

PREPARATIONS

Preparation 1

2-[4-(Methylsulfanyl)phenoxy]benzonitrile

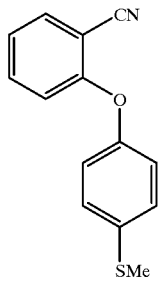

2-Fluorobenzonitrile (15.7 mL, 149 mmol) and 4-(methylsulfanyl)phenol (25 g, 178 mmol) were dissolved in DMF (500 mL) and $K_2CO_3$ (61.8 g, 447 mmol) was then added. The mixture was heated at 100° C. for 16 h under a nitrogen atmosphere. After cooling to room temperature the mixture was evaporated to dryness and then partitioned between ether (1 L) and water (2 L). The organic layer was separated, washed with 2M NaOH (500 mL), 10% (aq) $K_2CO_3$ (500 mL), dried ($MgSO_4$) and evaporated to give a light brown solid (35.62 g, 92%); $\delta_H$ ($CDCl_3$, 400 MHz) 2.50 (3H, s), 6.82 (1H, d), 7.05 (2H, d), 7.15 (1H, t), 7.30 (2H, m), 7.43 (1H, t), 7.62 (1H, d); MS m/z ($TS^+$) 259 ($MNH_4^+$).

Preparations 2–6

The following preparations were prepared by reacting the required phenol with either 4-chloro-3-iodonitrobenzene or the appropriate 2-fluorobenzonitrile according to the method of Preparation 1.

| Prep | T | $R^5$ | (aryl) | data |
|---|---|---|---|---|
| 2 | —CN | H | 4-$CF_3$-phenyl | $\delta_H$ ($CDCl_3$, 400 MHz) 6.96 (1H, d), 7.11 (2H, d), 7.21 (1H, m), 7.53 (1H, m), 7.63 (2H, d), 7.68 (1H, d) |
| 3 | —CN | H | 4-$OCF_3$-phenyl | $\delta_H$ ($CD_3OD$, 400 MHz) 6.99 (1H, d), 7.18 (2H, d), 7.27 (1H, m), 7.34 (2H, d), 7.62 (1H, t), 7.77 (1H, d); MS m/z ($TS^+$) 297 ($MNH_4^+$) |
| 4 | —CN | Br | indan-5-yl | $\delta_H$ ($CDCl_3$, 300 MHz) 2.15 (2H, quintet), 2.94 (4H, t), 6.76 (1H, d), 6.84 (1H, d), 6.95 (1H, s), 7.23 (1H, d), 7.54 (1H, dd), 7.76 (1H, d); MS m/z ($TS^+$) 331, 333 ($MNH_4^+$) |

-continued

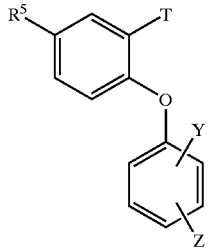

| Prep | T | R[5] | | data |
|---|---|---|---|---|
| 5 | —I[a] | —NO₂ | 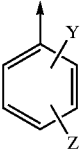 | $\delta_H$ (CDCl₃, 300 MHz) 6.80 (1H, m), 7.15 (2H, m), 7.35 (2H, m), 8.20 (1H, dd), .8.80 (1H, d) |
| 6 | —I[a] | —NO₂ | 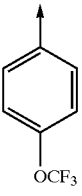 | $\delta_H$ (CDCl₃, 400 MHz) 2.32 (3H, s), 2.45 (3H, s), 6.70 (1H, d), 6.88 (2H, m), 7.18 (1H, d), 8.07 (1H, dd), 8.70 (1H, d); MS m/z (TS⁺) 419 (MNH₄⁺) |

[a]4-Chloro-3-iodonitrobenzene was synthesised according to J. Org. Chem. 1993, 58, 3194–3195.

Preparation 7

2-[4-(Methylsulfanyl)phenoxy]benzoic acid

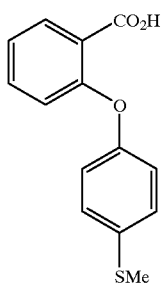

The nitrile of Preparation 1 (35.62 g, 148 mmol) was dissolved in EtOH (350 mL) and 6M NaOH (350 mL) was added. The mixture was heated at reflux for 16 h then allowed to cool to room temperature. The mixture was cooled in an ice bath and acidified to pH 1 with conc. HCl. The resulting precipitate was filtered and washed with water. After drying in a vacuum oven at 50° C. for 16 h this gave the title acid (38.29 g, 100%) as a white solid; $\delta_H$ (CD₃OD, 400 MHz) 2.42 (3H, s), 6.90 (2H, d), 6.99 (1H, d), 7.20 (1H, t), 7.24 (2H, m), 7.50 (1H, t), 7.90 (1H, d); MS m/z (ES−) 259 (M−H⁺).

Preparations 8–10

The following preparations were prepared from the appropriate precursor nitrites by the method of Preparation 7.

| Prep | Precursor | R⁵ | (Y/Z ring) | data |
|---|---|---|---|---|
| 8 | Prep 2 | H | 4-CF₃-phenyl | $\delta_H$ (CDCl₃, 400 MHz) 7.05 (3H, m), 7.30 (1H, m), 7.60 (3H, m), 8.13 (1H, d) |
| 9 | Prep 3 | H | 4-OCF₃-phenyl | $\delta_H$ (CD₃OD, 400 MHz) 6.97 (2H, d), 7.04 (1H, d), 7.22 (2H, d), 7.28 (1H, t), 7.54 (1H, t), 7.94 (1H, d); MS m/z (ES⁻) 297 (M-H⁺) |
| 10 | Prep 4 | Br | 2,3-dihydro-1H-inden-5-yl | MS m/z (ES⁻) 331, 333 (M-H⁺) |

Preparation 11

Ethyl 2-[4-(methylsulfanyl)phenoxy]benzoate

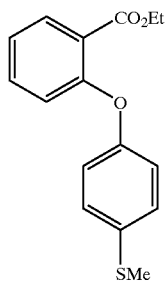

Concentrated H₂SO₄ (21 mL) was added to a mixture of the acid of Preparation 7 (38.29 g, 147 mmol) and ethanol (1470 mL) and the reaction was heated at reflux for 16 h under nitrogen. After cooling to room temperature the solvent was removed in vacuo and the residue was dissolved in EtOAc (1 L). Saturated NaHCO₃ (aq) (500 mL) was added followed by solid K₂CO₃ to basify to pH 8. The organic layer was separated and washed with saturated NaHCO₃ (aq) (500 mL), dried (MgSO₄) and evaporated to give a colourless oil (35.85 g, 85%); $\delta_H$ (CDCl₃, 400 MHz) 1.22 (3H, t), 2.42 (3H, s), 4.25 (2H, q), 6.83 (2H, d), 6.99 (1H, d), 7.20 (1H, t), 7.25 (2H, d), 7.43 (1H, t), 7.91 (1H, d); MS m/z (TS⁺) 289 (MH⁺).

Preparations 12–14

Preparations 12–14 were prepared from the appropriate acids by the method of Preparation 11.

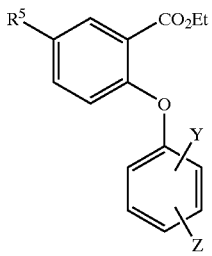

| Prep | Precursor | R⁵ | Y/Z | data |
|---|---|---|---|---|
| 12 | Prep 8 | H | 4-CF₃-phenyl | $\delta_H$ (DMSO-$d_6$, 400 MHz) 0.99 (3H, t), 4.07 (2H, q), 6.97 (2H, d), 7.22 (1H, d), 7.38 (1H, t), 7.66 (3H, m), 7.88 (1H, d) |
| 13 | Prep 9 | H | 4-OCF₃-phenyl | $\delta_H$ (CDCl₃, 400 MHz) 1.20 (3H, t), 4.14 (2H, q), 6.92 (2H, d), 7.03 (1H, d), 7.16 (2H, d), 7.24 (1H, m), 7.50 (1H, t), 7.95 (1H, d); MS m/z (TS⁺) 327 (MH⁺) |
| 14 | Prep 10 | Br | indanyl | $\delta_H$ (CDCl₃, 400 MHz) 1.25 (3H, t), 2.05 (2H, quintet), 2.83 (4H, t), 4.26 (2H, q), 6.70 (1H, d), 6.79 (2H, m), 7.12 (1H, d), 7.46 (1H, dd), 7.97 (1H, s); MS m/z (TS⁺) 362 (MH⁺) |

Preparation 15

3-Iodo-4-[4-(trifluoromethoxy)phenoxy]aniline

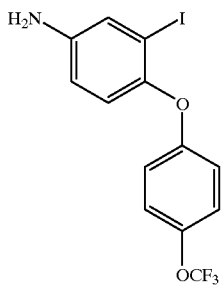

A mixture of the product from Preparation 5 (9.7 g), iron powder (11.49 g, 205 mmol) and CaCl₂ (1.14 g, 10.3 mmol) in EtOH (500 mL) and water (500 mL) was heated at reflux overnight. After cooling the mixture was filtered through a pad of Celite® and the solvent was removed in vacuo. The residue was partitioned between EtOAc (500 mL) and water (500 mL) and the organic layer was washed with brine, dried (MgSO₄) and evaporated to give a yellow oil (10.0 g) which was used without further purification; $\delta_H$ (CDCl₃, 300 MHz) 3.65 (2H, br), 6.70 (1H, m), 6.80–6.95 (3H, m), 7.20–7.05 (2H, m), 7.25 (1H, s); MS m/z (ES−) 396 (MH⁺).

Preparations 16–18

The following anilines were prepared according to the method of Preparation 15 by reduction of the appropriate nitro compounds.

| Prep | Precursor | T | Z | data |
|---|---|---|---|---|
| 16 | Prep 6 | I | 4-SMe, 3-Me phenyl | δ_H (CDCl₃, 400 MHz) 2.28 (3H, s), 2.37 (3H, s), 3.61 (2H, br), 6.60 (1H, m), 6.67 (1H, dd), 6.72 (1H, s), 6.78 (1H, d), 7.10 (1H, d), 7.15 (1H, d); MS m/z (TS⁺) 372 (MH⁺) |
| 17 | Prep 37 | N-Boc pyrrolidin-2-yl | 4-OCF₃ phenyl | δ_H (CDCl₃, 400 MHz) 1.27 and 143 (9H, 2 × s), 1.81 (3H, m), 2.20 (1H, m), 3.43–3.62 (4H, br), 4.84 and 4.99 (1H, 2 × m), 6.48 (1H, s), 6.54 (1H, d), 6.74 (1H, m), 6.83–6.98 (2H, m), 7.10 (2H, d); MS m/z (ES⁺) 439 (MH⁺) |
| 18 | Prep 38 | N-Boc pyrrolidin-2-yl | 4-CF₃ phenyl | δ_H (CDCl₃, 400 MHz) 1.26 and 1.39 (9H, 2 × s), 1.79 (3H, m), 2.14 (1H, m), 3.37–3.66 (4H, m), 4.78 and 4.90 (1H, 2 × m), 6.47 (1H, s), 6.53 (1H, d), 6.72 (1H, m), 6.93 (2H, m), 7.48 (2H, d); MS m/z (TS⁺) 423 (MH⁺) |

Preparation 19

N-{3-Iodo-4-[4-(trifluoromethoxy)phenoxy]phenyl}methanesulfonamide and N-{3-iodo-4-[4-(trifluoromethoxy)phenoxy]phenyl}-N-(methylsulfonyl)methanesulfonamide

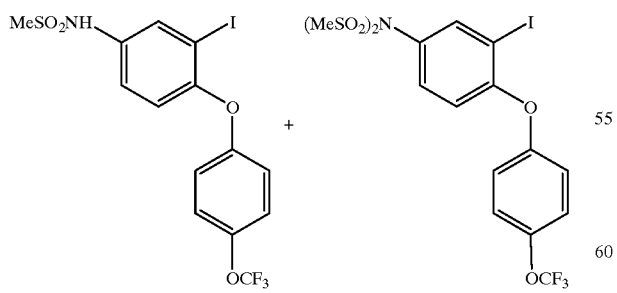

Methanesulfonyl chloride (2.13 mL, 27.5 mmol) was added to a solution of the aniline of Preparation 15 (10.0 g) and Et₃N (5.23 mL, 37.5 mmol) in DCM (250 mL) and the mixture was stirred at room temperature under N₂ overnight. The reaction mixture was washed with water (250 mL) and brine (250 mL), dried (MgSO₄) and evaporated to give a mixture of mono and bis sulfonamides as a yellow oil (12.4 g) which was used without further purification.

Preparation 20

N-{3-Iodo-4-[3-methyl-4-(methylsulfanyl)phenoxy]phenyl}methanesulfonamide and N-{3-iodo-4-[3-methyl-4-(methylsulfanyl)phenoxy]phenyl}-N-(methylsulfonyl)methanesulfonamide

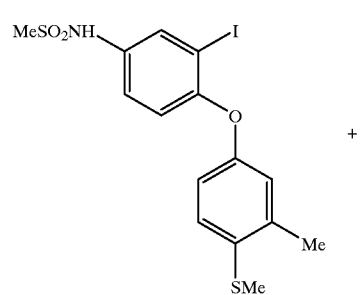

-continued

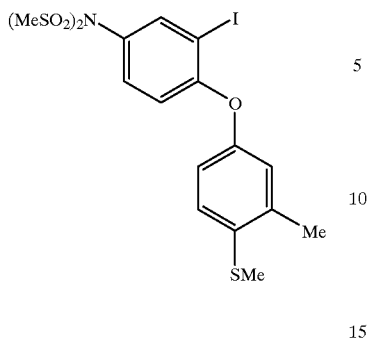

The title compounds were prepared from the aniline of Preparation 16 by the method of Preparation 19; MS m/z (TS⁺) 467 (MNH₄⁺, mono sulfonamide), 545 (MNH₄⁺, bis sulfonamide).

Preparation 21

Ethyl 5-[(methylsulfonyl)amino]-2-[4-(trifluoromethoxy)phenoxy]benzoate

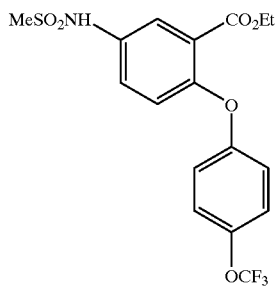

A mixture of the sulfonamides from Preparation 19 (5.0 g), Et₃N (2.2 mL, 15.7 mmol) and Pd(PPh₃)₄ (606 mg, 0.53 mmol) in EtOH (75 mL) was placed under CO (60 psi pressure) for 2 hrs. At this point tlc analysis indicated no reaction so a further portion of Pd(PPh₃)₄ (1.0 g, 0.87 mmol) was added and the mixture was heated at 100° C. under CO (60 psi pressure) overnight. After cooling the mixture was filtered through a pad of Celite® and the solvent was removed in vacuo. The residue was partitioned between EtOAc and water and the organic layer was washed with brine, dried (MgSO₄) and evaporated to give a crude product (3.1 g) which was used without further purification; $\delta_H$ (CDCl₃, 300 MHz) 1.20 (3H, t), 3.06 (3H, s), 4.27 (2H, q), 6.95 (3H, m), 7.05 (1H, d), 7.20 (2H, d), 7.50 (1H, dd), 7.80 (1H, d).

Preparation 22

Ethyl 2-[3-methyl-4-(methylsulfanyl)phenoxy]-5-[(methylsulfonyl)amino]benzoate

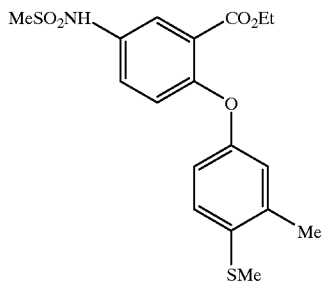

The title compound was prepared by the method of Preparation 21 from the sulfonamides of Preparation 20; $\delta_H$ (CDCl₃, 300 MHz) 1.27 (3H, t), 2.34 (3H, s), 2.43 (3H, s), 3.05 (3H, s), 4.32 (2H, q), 6.79 (2H, m), 6.98 (1H, d), 7.18 (1H, d), 7.44 (1H, dd), 7.75 (1H, d); MS m/z (TS⁺) 396 (MH⁺).

Preparation 23

3-{2-[4-(Methylsulfanyl)phenoxy]benzoyl}-1-vinyl-2-pyrrolidinone

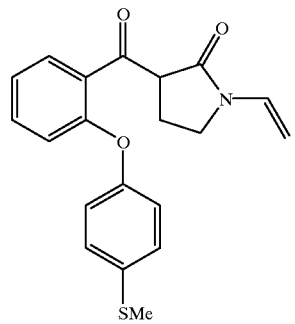

LiHMDS (1M solution in THF, 167 mL, 167 mmol) was cooled to −25° C. and 1-vinyl-2-pyrrolidinone (10.66 mL, 100 mmol) was added rapidly. A solution of the ester of Preparation 11 (24.02 g, 83.3 mmol) in THF (278 mL) was then added dropwise, keeping the temperature below −20° C. The mixture was allowed to warm to room temperature over 2 hrs and then stirred for 4.5 days. Saturated NH₄Cl (aq) (400 mL) was added and the mixture was stirred for 10 min. The organic solvent was removed in vacuo and EtOAc (900 mL) was added. The layers were separated and the organic layer was washed with water (2 L), dried (MgSO₄) and evaporated to give a brown oil. Purification by filtering through silica (eluting with 2:1:1 DCM:pentane:EtOAc) gave the product as a brown oil as a mixture of tautomers (28.44 g, 97%); MS m/z (TS⁺) 354 (MH⁺).

Preparations 24–28

The following pyrrolidinones were prepared according to the method of Preparation 23 starting from the appropriate esters.

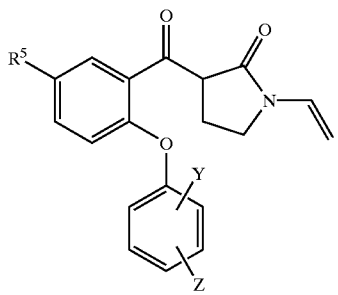

| Prep | Precursor | R⁵ | 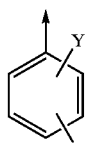 Z | data |
|---|---|---|---|---|
| 24 | Prep 12 | H | 4-CF₃-phenyl | MS m/z (TS⁺) 376 (MH⁺) |
| 25 | Prep 13 | H | 4-OCF₃-phenyl | δ_H (CDCl₃, 400 MHz) (3:1 mixture of tautomers A:B) 2.30 (1H, m, A), 2.66 (1H, m, A), 2.77 (2H, t, B), 3.44–3.64 (2H, m), 4.38–4.50 (2H, m), 4.69 (1H, m, A), 6.87 (1H, d, A), 6.95–7.02 (1H(A) + 2H(B), m), 7.08–7.27 (5H, m), 7.40 (1H, m, B), 7.46 (1H, m, A), 7.58 (1H, d, B), 7.82 (1H, d, A), 11.96 (1H, br, B); MS m/z (TS⁺) 392 (MH⁺) |
| 26 | Prep 14 | Br | indanyl | δ_H (CDCl₃, 400 MHz) (3:1 mixture of tautomers A:B) 2.07 (2H, quintet), 2.28 (1H, m, A), 2.59 (1H, m, A), 2.76 (2H, t, B), 2.85 (4H, m), 3.40–3.60 (2H, m), 4.35–4.46 (2H, m), 4.75 (1H, m, A), 6.65–6.74 (1H(A) + 2H(B), m), 6.79–6.86 (1H, m), 6.93–7.01 (2H, m, A), 7.05–7.14 (2H, m, B), 7.18 (1H, d, A), 7.37 (1H, dd, B), 7.43 (1H, dd, A), 7.64 (1H, d, B), 7.82 (1H, d, B), 11.99 (1H, br, B); MS m/z (TS⁺) 426, 428 (MH⁺) |
| 27 | Prep 21 | —NHSO₂Me | 4-OCF₃-phenyl | MS m/z (TS⁺) 502 (MNH₄⁺) |
| 28 | Prep 22 | —NHSO₂Me | 3-Me-4-SMe-phenyl | δ_H (CDCl₃, 400 MHz) (3:1 mixture of tautomers A:B) 2.30 (3H, s), 2.38–2.47 (3H, s + 1H, m, A), 2.59 (1H, m, A), 2.76 (2H, t, B), 2.96 (3H, s, A), 2.99 (3H, s, B), 3.41–3.62 (2H, m), 4.37–4.48 (2H, m), 4.73 (1H, m, A), 6.74–7.18 (5H, m), 7.38 (1H, m), 7.48 (1H, s), 12.04 (1H, br, B) |

[a]3 Equivalents of LiHMDS were used instead of 2.

Preparation 29

5-{2-[4-(Methylsulfanyl)phenoxy]phenyl}-3,4-dihydro-2H-pyrrole

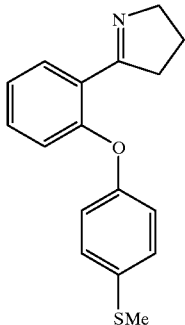

A solution of the product of Preparation 23 (28.44 g, 80.48 mmol) in dioxane (200 mL) was added dropwise over 1 hr to 6M HCl (600 mL) at reflux and the mixture was heated at reflux for a further 16 hrs. After cooling the organic solvent was removed in vacuo and the residue was basified to pH 11 with 6M NaOH. The product was extracted with EtOAc (1 L) and the organic layer was then washed with sat NaHCO$_3$ (aq) dried (MgSO$_4$) and evaporated to give a brown oil (33.04 g) which was used without further purification; δ$_H$ (CDCl$_3$, 400 MHz) 1.92 (2H, m), 2.45 (3H, s), 2.98 (2H, t), 3.98 (2H, t), 6.87 (3H, m), 7.18 (1H, t), 7.25 (2H, d), 7.38 (1H, t), 7.95 (1H, d); MS m/z (TS$^+$) 284 (MH$^+$).

Preparations 30–34

The following pyrrolines were prepared according to the method of Preparation 29 starting from the appropriate pyrrolidinones.

| Prep | Precursor | R$^5$ | Z | data |
|---|---|---|---|---|
| 30 | Prep 24 | H | 4-CF$_3$-phenyl | MS m/z (TS$^+$) 306 (MH$^+$) |
| 31 | Prep 25 | H | 4-OCF$_3$-phenyl | δ$_H$ (CDCl$_3$, 400 MHz) 1.94 (2H, m), 2.94 (2H, m), 3.95 (2H, m), 6.93 (3H, m), 7.12–7.22 (3H, m), 7.39 (1H, m), 7.96 (1H, d) |
| 32 | Prep 26 | Br | indan-5-yl | δ$_H$ (CDCl$_3$, 400 MHz) 1.92 (2H, quintet), 2.07 (2H, quintet), 2.83 (4H, t), 2.97 (2H, m), 3.94 (2H, m), 6.72 (2H, m), 6.78 (1H, s), 7.13 (1H, d), 7.38 (1H, dd), 8.07 (1H, s) |

-continued

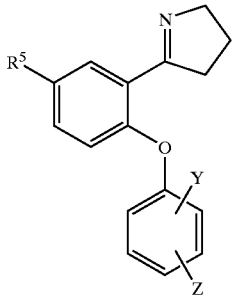

| Prep | Precursor | R⁵ | Y/Z ring | data |
|---|---|---|---|---|
| 33 | Prep 27 | —NHSO₂Me | (4-OCF₃ phenyl) | $\delta_H$ (CDCl₃, 400 MHz) 1.95 (2H, m), 2.90 (2H, m), 3.00 (3H, s), 3.90 (2H, t), 6.90 (3H, m), 7.19 (2H, d), 7.40 (1H, dd), 7.68 (1H, d); MS m/z (ES⁺) 415 (MH⁺). |
| 34 | Prep 28 | —NHSO₂Me | (4-SMe, 3-Me phenyl) | $\delta_H$ (CDCl₃, 300 MHz) 1.99 (2H, quintet), 2.36 (3H, s), 2.47 (3H, s), 2.96–3.04 (3H, s + 2H, m), 3.98 (2H, t), 6.73 (1H, br), 6.81 (2H, m), 6.92 (1H, d), 7.19 (1H, d), 7.40 (1H, dd), 7.74 (1H, d) |

Preparation 35

2-{2-[4-(Methylsulfanyl)phenoxy]phenyl}-1-(trifluoroacetyl)pyrrolidine

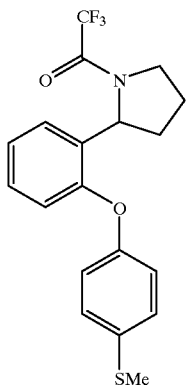

Et₃N (9.25 mL, 66.4 mmol) was added to a solution of the amine of Example 1 (5.34 g, 16.6 mmol) in DCM (66 mL), cooled with an ice bath, followed by trifluoroacetic anhydride (4.69 mL, 33.2 mmol). The mixture was stirred at room temperature for 2 h then concentrated in vacuo. The residue was dissolved in toluene and evaporated then dissolved in EtOAc and evaporated to give a brown oil which was used without further purification; MS m/z (TS⁺) 399 (MNH₄+).

Preparation 36

2-{2-[4-(Trifluoromethyl)phenoxy]phenyl}-1-(trifluoroacetyl)pyrrolidine

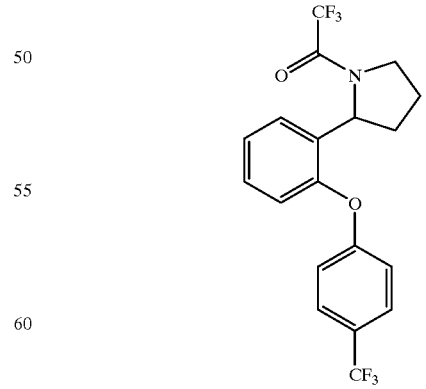

The title compound was prepared from the pyrrolidine of Example 2 by the method of Preparation 35; MS m/z (TS⁺) 421 (MNH₄+).

Preparation 37 tert-Butyl 2-{5-nitro-2-[4-(trifluoromethoxy)phenoxy]phenyl}-1-pyrrolidinecarboxylate

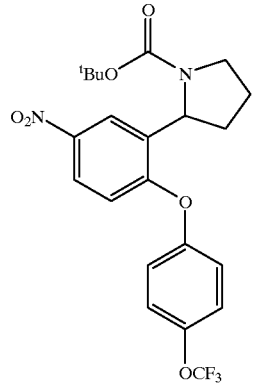

(Boc)$_2$O (8.12 g, 37.2 mmol) was added portionwise to a solution of the amine of Example 16 (22.2 mmol) in DCM (350 mL) and the mixture was stirred at room temperature for 16 h. The mixture was diluted with DCM (650 mL), washed with 10% aq K$_2$CO$_3$ (1 L) and the organic layer was dried (MgSO$_4$) and evaporated. The residue was purified by column chromatography [SiO$_2$; pentane increasing polarity to 7.5% EtOAc in pentane] to give the desired product (6.61 g, 64%) as a yellow solid; $\delta_H$ (CDCl$_3$, 400 MHz) (mixture of rotamers) 1.21 and 1.43 (9H, 2×s), 1.96 (3H, m), 2.37 (1H, br), 2.53 and 3.65 (2H, 2×m), 5.10 and 5.26 (1H, 2xm), 6.70–6.82 (1H, m), 6.97–7.11 (2H, m), 7.23 (2H, m), 7.98–8.11 (2H, m); MS m/z (ES$^+$) 469 (MH$^+$).

Preparation 38 tert-Butyl 2-{5-nitro-2-[4-(trifluoromethyl)phenoxy]phenyl}-1-pyrrolidinecarboxylate

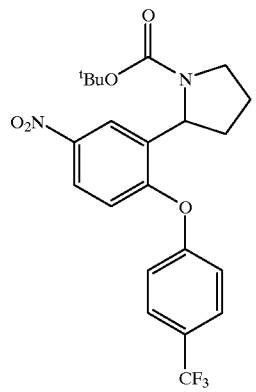

The title compound was prepared from the nitro compound of Example 17 using the method of Preparation 37; $\delta_H$ (CDCl$_3$, 400 MHz) (mixture of rotamers) 1.22 and 1.44 (9H, 2×s), 1.87 (3H, m), 2.35 (1H, m), 3.46–3.70 (2H, m), 5.07 and 5.22 (1H, 2×m), 6.78–6.91 (1H, m), 7.03–7.17 (2H, m), 7.64 (2H, m), 7.99–8.14 (2H, m); MS m/z (TS$^+$) 453 (MH$^+$).

Preparation 39 tert-Butyl 2-(2-[4-(trifluoromethoxy)phenoxy]-5-{[(trifluoromethyl)sulfonyl]amino}phenyl)-1-pyrrolidinecarboxylate

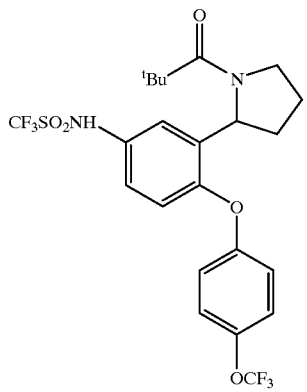

Trifluoromethanesulfonic anhydride (412,L, 2.51 mmol) was added to a solution of the aniline of Preparation 17 (1.0 g, 2.28 mmol) and Et$_3$N (636 μL, 4.56 mmol) in DCM (23 mL) at −78° C. and the mixture was slowly allowed to warm to room temperature. The reaction mixture was quenched with 10% aq K$_2$CO$_3$ (50 mL), diluted with water (50 mL) and DCM (50 mL) and the layers were separated. The organic layer was dried (MgSO$_4$) and evaporated to give a brown oil. This was purified by column chromatography [SiO$_2$; 1% (9:1 MeOH:880 NH$_3$) in DCM] to give the desired product (1.13 g, 87%) as a light brown foam; $\delta_H$ (CD$_3$OD, 400 MHz) (mixture of rotamers) 1.25 and 1.45 (9H, 2×s), 1.86 (3H, m), 2.28 (1H, m), 3.47–3.63 (2H, m), 5.02 and 5.12 (1H, 2×m), 6.85 and 6.95 (1H, 2×m), 7.02 (1H, d), 7.12 and 7.20 (3H, 2×m), 7.27 (2H, d); MS m/z (ES$^-$) 569 (M−H$^+$).

Preparation 40 tert-Butyl 2-{5-[(methylsulfonyl)amino]-2-[4-(trifluoromethoxy)phenoxy]phenyl}-1-pyrrolidinecarboxylate (enantiomer 1) and

Preparation 41 tert-Butyl 2-{5-[(methylsulfonyl)amino]-2-[4-(trifluoromethoxy)phenoxy]phenyl}-1-pyrrolidinecarboxylate (enantiomer 2)

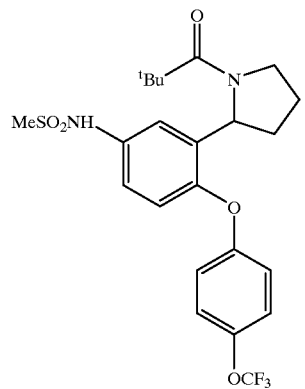

Methanesulfonyl chloride (2 mL, 30.7 mmol) was added dropwise to a solution of the aniline of Preparation 17 (6.1 g, 14.0 mmol) and Et$_3$N (4.9 mL, 34.9 mmol) in DCM (56 mL) and the mixture was stirred at room temperature under N₂ overnight. The reaction mixture was evaporated, dissolved in 1,4-dioxane (70 mL) and treated with 6M NaOH (35 mL). After stirring at room temperature for 2 h the reaction mixture was concentrated in vacuo and the aqueous residue was diluted with water (400 mL). EtOAc (500 mL) was added and the mixture was acidified to pH 2 with conc. HCl. The organic layer was separated, washed with sat. aq NaHCO₃, dried (MgSO₄) and evaporated to give a brown foam (6.05 g, 84%) which was used without further purification; $\delta_H$ (CD₃OD, 400 MHz) (mixture of rotamers) 1.26 and 1.46 (9H, 2×s), 1.88 (3H, m), 2.27 (1H, m), 2.91 and 2.95 (3H, 2×s), 3.47–3.62 (2H, m), 5.00 and 5.06 (1H, 2×m), 6.84–7.28 (7H, m); MS m/z (TS⁺) 534 (MNH₄⁺). The enantiomers were separated on a Chiralpak® AD250×20 mm chiral column using 80% hexane/20% IPA as an eluent to give Preparation 40 (retention time 4.9 min) and Preparation 41 (retention time 6.5 min).

Preparation 42 tert-Butyl 2-{5-[(methylsulfonyl)amino]-2-[4-(trifluoromethylphenoxy)phenyl}-1-pyrrolidinecarboxylate

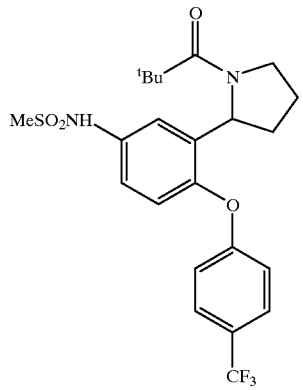

The title compound was prepared from the aniline of Preparation 18 by the method of Preparations 40 and 41; $\delta_H$ (CDCl₃, 400 MHz) (mixture of rotamers) 1.27 and 1.41 (9H, 2×s), 1.81 (3H, m), 2.22 (1H, m), 2.97 and 3.00 (3H, 2×s), 3.40–3.60 (2H, m), 4.93 and 5.04 (1H, 2×m), 6.50 (1H rotamer A, br), 6.80–7.10 (5H, m +1H rotamer B), 7.53 (2H, d); MS m/z (TS⁺) 518 (MNH₄⁺).

Preparation 43 tert-Butyl 2-{5-[methyl(methylsulfonyl)amino]-2-[4-(trifluoromethoxy)phenoxy]phenyl}-1-pyrrolidinecarboxylate

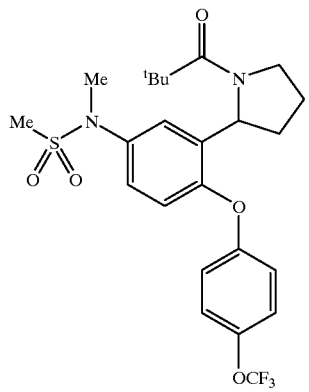

MeI (934 μL, 15 mmol) was added to a mixture of K₂CO₃ (456 mg, 3.3 mmol) and Preparations 40 and 41 (1.55 g, 3.0 mmol) in acetonitrile (15 mL) and the reaction was stirred at room temperature for 60 h before being concentrated to low volume. The reaction mixture was diluted with 2M NaOH (100 mL) and EtOAc (100 mL) and the layers were separated. The organic layer was washed with sat aq NaHCO₃, dried (MgSO₄) and evaporated to give a brown oil containing EtOAc (2.12 g, assumed quantitative yield) which crystallised on standing. This material was used without further purification; $\delta_H$ (CD₃OD, 400 MHz) (mixture of rotamers) 1.26 and 1.45 (9H, 2×s), 1.87 (3H, m), 2.30 (1H, m), 2.87 and 2.92 (3H, 2×s), 3.28 and 3.30 (3H, 2×s), 3.49–3.67 (2H, m), 5.03 and 5.10 (1H, 2×m), 6.87 and 6.96 (1H, 2×m), 7.04 and 7.13 (2H, 2×d), 7.20–7.35 (4H, m); MS m/z (ES⁺) 553 (MH⁺).

Preparation 44

3-(1-Formyl-2-pyrrolidinyl)-4-[4-(methylsulfanyl)phenoxy]benzenesulfonamide (enantiomer 1)

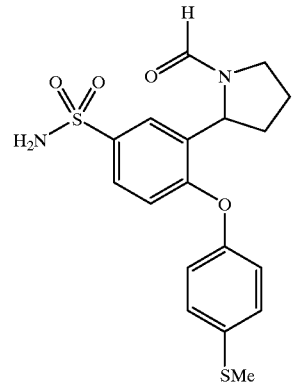

Dicyclohexylcarbodiimide (137 mg, 0.66 mmol) was added to a solution of pentafluorophenol (123 mg, 0.67 mmol) in ether (3 mL) followed by formic acid (28 μL, 0.74 mmol). The mixture was stirred for 1 h and then filtered, washing the residue with ether. The filtrate was concentrated to ~2 mL and a solution of the hydrochloride salt of Example 6 (88 mg, 0.22 mmol) and Et₃N (33 μL, 0.24 mmol) in DCM (1 mL) was added. The mixture was stirred for 16 h then concentrated to low volume and partitioned between water (25 mL) and DCM (25 mL). The organic layer was dried (MgSO₄) and evaporated to give a clear oil (93 mg, assumed quantitative yield) which was used without further purification; $\delta_H$ (CD₃OD, 400 MHz) (mixture of rotamers) 1.90–2.14(3H, m), 2.37–2.53 (4H, m), 3.67 and 3.83 (2H, 2×m), 5.32 and 5.42 (1H, 2×m), 6.87 (1H, m), 7.04 (2H, m), 7.36 (2H, m), 7.69–7.78 (2H, m), 8.16 and 8.36 (1H, 2×m).

Preparation 45

3-(1-Formyl-2-pyrrolidinyl)-4-[4-(methylsulfanyl)phenoxy]benzenesulfonamide (enantiomer 2)

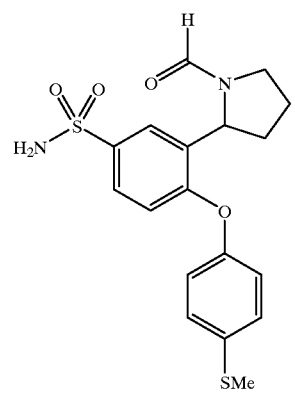

The title compound was prepared from the hydrochloride salt of Example 7 by the method of Preparation 44; $\delta_H$ (CD$_3$OD, 400 MHz) (mixture of rotamers) 1.90–2.14(3H, m), 2.37–2.53 (4H, m), 3.67 and 3.83 (2H, 2×m), 5.32 and 5.42 (1H, 2×m), 6.87 (1H, m), 7.04 (2H, m), 7.36 (2H, m), 7.69–7.78 (2H, m), 8.16 and 8.36 (1H, 2×m); MS m/z (TS$^+$) 410 (MNH$_4^+$).

Biological Activity

A number of compounds were tested for biological activity by their ability to inhibit the uptake of serotonin by human serotonin transporters as follows.

(i) Cell Culture

Human embryonic kidney cells (HEK-293) stably transfected with either the human serotonin transporter (hSERT), noradrenaline transporter (hNET) or dopamine transporter (hDAT) were cultured under standard cell culture techniques (cells were grown at 37° C. and 5% CO$_2$ in DMEM-culture media (supplemented with 10% dialysed foetal calf serum (FCS), 2 mM I-glutamine and 250 μg/ml geneticin)). Cells were harvested for the assay to yield a cell suspension of 750,000 cells/ml.

(i) Determination of Inhibitor Potency

All test compounds were dissolved in 100% DMSO and diluted down in assay buffer to give appropriate test concentrations. Assays were carried out in 96-well filter bottom plates. Cells (7500 cells/assay well) were pre-incubated in standard assay buffer containing either test compound, standard inhibitor or compound vehicle (1% DMSO) for 5 minutes. Reactions were started by addition of either $^3$H-Serotonin, $^3$H-Noradrenaline or $^3$H-Dopamine substrates. All reactions were carried out at room temperature in a shaking incubator. Incubation times were 5 minutes for the hSERT and hDAT assays and 15 minutes for the hNET assay. Reactions were terminated by removal of the reaction mixture using a vacuum manifold followed by rapid washing with ice cold assay buffer. The quantity of $^3$H-substrate incorporated into the cells was then quantified.

Assay plates were dried in a microwave oven, scintillation fluid added, and radioactivity measured. Potency of test compounds was quantified as IC$_{50}$ values (concentration of test compound required to inhibit the specific uptake of radiolabelled substrate into the cells by 50%).

(iii) Standard Assay Buffer Composition:
Trizma hydrochloride (26 mM)
NaCl (124 mM)
KCl (4.5 mM)
KH$_2$PO$_4$ (1.2 mM)
MgCl$_2$.6H$_2$O (1.3 mM)
Ascorbic acid (1.136 mM)
Glucose (5.55 mM)
pH 7.40
CaCl$_2$ (2.8 mM)
Pargyline (100 μM)

Note: The pH of the buffer was adjusted to 7.40 with 1 M NaOH before addition of CaCl$_2$ and pargyline.

(iv) Summary of Assay Parameters

| | hSERT Assay | hDAT Assay | hNET Assay |
|---|---|---|---|
| Cell concentration per assay well. | 75,000 | 75,000 | 75,000 |
| Substrate Concentration. | $^3$H-5HT (50 nM) | $^3$H-Dopamine (200 nM) | $^3$H-Noradrenaline (200 nM) |
| Incubation time (minutes) | 5 | 5 | 15 |

Compounds having a serotonin re-uptake inhibition (SRI) IC$_{50}$ value of less than or equal to 100 nM include the title compounds of Examples 1, 3–12, 14 and 18–22.

Compounds having an serotonin re-uptake inhibition (SRI) IC$_{50}$ value of less than or equal to 100 nM and which are more than 10-fold as potent in the inhibition of serotonin re-uptake than in the inhibition of dopamine re-uptake or noradrenaline re-uptake include the title compounds of Examples 1, 3, 4, 6–11, 14 and 18–22.

Compounds having an serotonin re-uptake inhibition (SRI) IC$_{50}$ value of less than or equal to 100 nM and which are more than 100-fold as potent in the inhibition of serotonin re-uptake than in the inhibition of dopamine re-uptake or noradrenaline re-uptake include the title compounds of Examples 3, 4, 7–11, 14 and 18–22.

Compounds having an serotonin re-uptake inhibition (SRI) IC$_{50}$ value of less than or equal to 100 nM and which are more than 100-fold as potent in the inhibition of serotonin re-uptake than in the inhibition of dopamine re-uptake and noradrenaline re-uptake include the title compounds of Examples 7, 11 and 22.

Compounds having an serotonin re-uptake inhibition (SRI) IC$_{50}$ value of less than or equal to 50 nM and which are more than 100-fold as potent in the inhibition of serotonin re-uptake than in the inhibition of dopamine re-uptake and noradrenaline re-uptake include the title compounds of Examples 7, 11 and 22.

In particular, the title compound of Example 7 had a serotonin re-uptake inhibition (SRI) IC$_{50}$ of 5.4 nM; the title compound of Example 11 had a serotonin re-uptake inhibition (SRI) IC$_{50}$ of 5.9 nM and the title compound of Example 21 had a serotonin re-uptake inhibition (SRI) IC$_{50}$ of 13 nM.

What is claimed is:

1. A compound of formula (I), or a pharmaceutically acceptable salt, solvate or polymorph thereof;

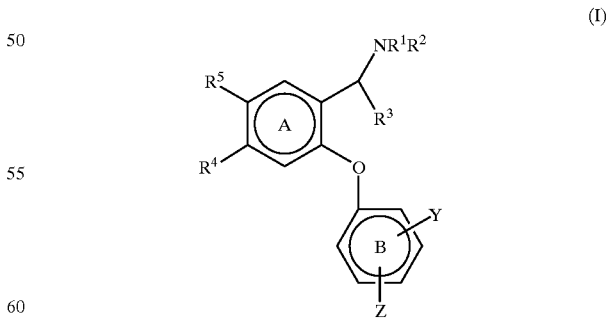

wherein:
R$^1$ is H or C$_1$-C$_6$ alkyl;
R$^2$ and R$^3$, together with the interconnecting atoms thereof form a pyrrolidine ring;

Z is $CF_3$, $OCF_3$, $C_1$–$C_6$alkylthio or $C_1$–$C_6$alkoxy;

Y is hydrogen, halogen, —$OR^a$, $R^a$ or $C_1$–$C_6$alkylthio, and wherein $R^a$ is $C_1$–$C_4$ alkyl optionally substituted with fluorine atoms;

or when Z and Y are attached para and meta to the ether linkage linking rings A and B, Z and Y are linked so that, together with the interconnecting atoms, Z and Y form a fused 5 to 7-membered carbocyclic or heterocyclic ring which may be saturated, unsaturated or aromatic, and wherein when Z and Y form a heterocyclic ring, in addition to carbon atoms, the linkage contains one or two heteroatoms independently selected from oxygen, sulfur and nitrogen;

$R^4$ and $R^5$, which may be the same or different, are:
A—X, wherein A=—CH=CH— or —$(CH_2)_p$— where p is 0, 1 or 2; X is hydrogen, F, Cl, Br, I, $CONR^6R^7$, $SO_2NR^6R^7$, $SO_2NHC(=O)R^6$, OH, $C_{1-4}$alkoxy, $NR^8SO_2R^9$, $NO_2$, $NR^6R^{11}$, CN, $CO_2R^{10}$, CHO, $SR^{10}$, $S(O)R^9$ or $SO_2R^{10}$; $R^6$, $R^7$, $R^8$ and $R^{10}$ which may be the same or different, are hydrogen or $C_{1-6}$alkyl optionally substituted independently by one or more $R^{12}$; $R^9$ is $C_{1-6}$alkyl optionally substituted independently by one or more $R^{12}$; $R^{11}$ is hydrogen, $C_{1-6}$ alkyl optionally substituted independently by one or more $R^{12}$, $C(O)R^6$, $CO_2R^9$, $C(O)NHR^6$ or $SO_2NR^6R^7$; $R^{12}$ is F, OH, $CO_2H$, $C_{3-6}$cycloalkyl, $NH_2$, $CONH_2$, $C_{1-6}$alkoxy, $C_{1-6}$alkoxycarbonyl or a 5- or 6-membered heterocyclic ring containing 1, 2 or 3 heteroatoms selected from N, S and O optionally substituted independently by one or more $R^{13}$; or $R^6$ and $R^7$, together with the nitrogen to which they are attached, form a 4-, 5- or 6-membered heterocyclic ring optionally substituted independently by one or more $R^{13}$; or a 5- or 6-membered heterocyclic ring containing 1, 2 or 3 heteroatoms selected from N, S and O, optionally substituted independently by one or more $R^{13}$; wherein $R^{13}$ is hydroxy, $C_1$–$C_4$alkoxy, F, $C_1$–$C_6$alkyl, haloalkyl, haloalkoxy, —$NH_2$, —$NH(C_1$–$C_6$alkyl) or —$N(C_1$–$C_6$alkyl)_2$ with the proviso that $R^4$ and $R^5$ are not both hydrogen.

2. A compound according to claim 1, or a pharmaceutically acceptable salt, solvate or polymorph thereof, wherein $R^1$ is hydrogen or methyl.

3. A compound according to claim 1, or a pharmaceutically acceptable salt, solvate or polymorph thereof, wherein at least one of Z or Y is para to the ether linkage linking ring A and ring B and is not hydrogen.

4. A compound according to claim 3, or a pharmaceutically acceptable salt, solvate or polymorph thereof, wherein the other Z or Y is meta to the ether linkage linking ring A and ring B.

5. A compound according to claim 1, or a pharmaceutically acceptable salt, solvate or polymorph thereof, wherein Z is $CF_3$, $OCF_3$, SMe, SEt or OMe;

Y is hydrogen, F, Cl, Br, methyl, ethyl, OMe, SMe or SEt; or when Z and Y are attached para and meta to the ether linkage linking rings A and B, Z and Y are linked so that, together with the interconnecting atoms thereof, Z and Y form a fused 5 or 6-membered carbocyclic or heterocyclic ring which may be saturated, unsaturated or aromatic, and wherein when Z and Y form a heterocyclic ring, in addition to carbon atoms; the linkage contains one or two heteroatoms independently selected from oxygen, sulfur and nitrogen.

6. A compound according to claim 1, or a pharmaceutically acceptable salt, solvate or polymorph thereof, wherein $R^4$ and $R^5$, which may be the same or different, are —$(CH_2)_p$—X, where p is 0, 1 or 2; X is hydrogen, hydroxy, $CONR^6R^7$, $SO_2NR^6R^7$, $NR^8SO_2R^9$, $SR^{10}$, $SOR^9$ or $SO_2R^{10}$ wherein $R^6$, $R^7$, $R^8$, $R^9$ and $R^{10}$ are as defined in claim 1, or a 5- or 6-membered heterocyclic ring containing 1, 2 or 3 heteroatoms selected from N, S and O.

7. A compound according to claim 1, or a pharmaceutically acceptable salt, solvate or polymorph thereof, wherein $R^4$ and $R^5$, which may be the same or different, are:

—$(CH_2)_p$—X, where p is 0 or 1; X is hydrogen, hydroxy, $CONR^6R^7$, $SO_2NR^6R^7$ or $NR^8SO_2R^9$; wherein $R^6$ and $R^7$, which may be the same or different, are hydrogen or $C_1$–$C_3$alkyl optionally substituted by hydroxy, —$CONH_2$ or $C_1$–$C_3$alkoxy; $R^8$ is hydrogen, hydroxyethyl or methyl; or $R^9$ is methyl, ethyl, isopropyl, trifluoromethyl or methoxyethyl; or triazolyl, imidazolyl or pyrazolyl.

8. A compound according to claim 1, or a pharmaceutically acceptable salt, solvate or polymorph thereof, wherein $R^4$ is hydrogen.

9. A compound according to claim 1, or a pharmaceutically acceptable salt, solvate or polymorph thereof, selected from the group:

(+) 4-[4-(methylsulfanyl)phenoxy]-3-(2-pyrrolidinyl)benzenesulfonamide hydrochloride;

N-methyl-4-[4-(methylsulfanyl)phenoxy]-3-(2-pyrrolidinyl)benzenesulfonamide;

N-methyl-N-{3-(2-pyrrolidinyl)-4-[4-(trifluoromethoxy)phenoxy]phenyl}-methanesulfonamide; and (+) N-{3-(2-pyrrolidinyl)-4-[4-(trifluoromethoxy)phenoxy]phenyl}-methanesulfonamide.

10. A pharmaceutical formulation comprising a compound as defined in claim 1, or a pharmaceutically acceptable salt, solvate or polymorph thereof, and a pharmaceutically acceptable adjuvant, diluent carrier.

11. A method of treatment of a disorder in which the regulation of monoamine transporter function is implicated, comprising the administration of an effective amount of a compound as defined in claim 1, pharmaceutically acceptable salt, solvate or polymorph thereof, to a patient in need of such treatment.

12. A method of treatment of premature ejaculation, comprising the administration of an effective amount of a compound as defined in claims 1, pharmaceutically acceptable salt, solvate or polymorph thereof, to a patient in need of such treatment.

13. A method of increasing ejaculatory latency which comprises the administration of an effective amount of a compound as defined in claim 1, pharmaceutically acceptable salt, solvate or polymorph thereof, to a male desiring increased ejaculatory latency.

14. A process for preparing a compound of formula (Ia), wherein R4, R5, Y and Z are as defined in claim 1

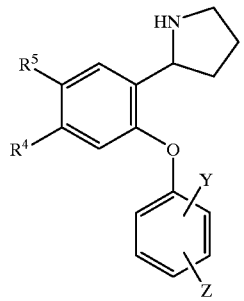
(Ia)

comprising reacting a compound of formula II

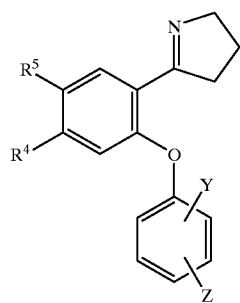
(II)

with a hydride reducing agent in a suitable solvent.

15. A process according to claim 14 further comprising the step of reacting a compound of formula III

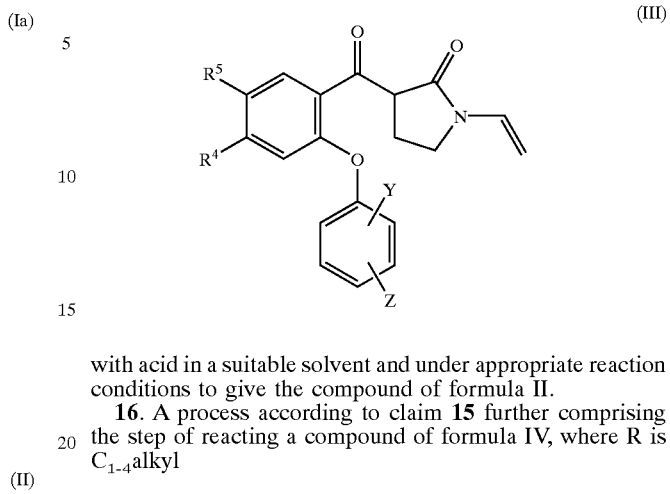
(III)

with acid in a suitable solvent and under appropriate reaction conditions to give the compound of formula II.

16. A process according to claim 15 further comprising the step of reacting a compound of formula IV, where R is $C_{1-4}$alkyl

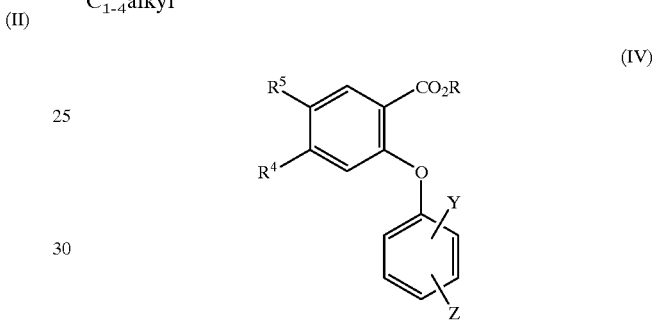
(IV)

with the anion of 1-vinyl-2-pyrrolidinone to give the compound of formula III.

* * * * *